(12) United States Patent
Meyers

(10) Patent No.: US 6,479,268 B1
(45) Date of Patent: Nov. 12, 2002

(54) 7970, A NOVEL ATPASE-LIKE MOLECULE AND USES THEREOF

(75) Inventor: Rachel A. Meyers, Newton, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/790,179

(22) Filed: Feb. 21, 2001

Related U.S. Application Data

(60) Provisional application No. 60/185,609, filed on Feb. 29, 2000.

(51) Int. Cl.$^7$ ............................. C12N 9/12; C12N 15/54
(52) U.S. Cl. ............................ 435/194; 435/6; 435/325; 536/23.2
(58) Field of Search ............................. 435/320.1, 325, 435/144, 6, 975; 536/23.2

(56) References Cited

U.S. PATENT DOCUMENTS 5,932,444 A    8/1999   Hillman et al.

FOREIGN PATENT DOCUMENTS

| WO | WO 9845437 | * 10/1998 |
| WO | WO00/55174 A1 | 9/2000 |

OTHER PUBLICATIONS

Strausberg, R., AI796091, 1999.*
Smith, D.R., et al. YL15, 1995.*
Smith, D.R., et al. S72845, 1997.*
GenBank Report for Accession No. AAF02877, Direct Submission on Aug. 26, 1999.
GenBank Report for Accession No. AAF44893, Direct Submission on Mar. 8, 2000.
GenBank Report for Accession No. AAF76434, Direct Submission on Nov. 16, 1999.
GenBank Report for Accession No. AB029006, Direct Submission on Jun. 17, 1999.
GenBank Report for Accession No. AC005454, Direct Submission on Aug. 14, 1998.
GenBank Report for Accession No. AC006263 Direct Submission on Dec. 30, 1998.
GenBank Report for Accession No. AI796091. (1999).
GenBank Report for Accession No. AJ246001, Direct Submission Jun. 17, 1999.
GenBank Report for Accession No. AJ246002, Direct Submission on Jun. 17, 1999.
GenBank Report for Accession No. AJ251819, Direct Submission on Dec. 14, 1999.
GenBank Report for Accession No. AP000005, Direct Submission on Jun. 11, 1998.
GenBank Report for Accession No. AU080226. (2000).
GenBank Report for Accession No. BAB09730, Direct Submission on Jun. 17, 1998.
GenBank Report for Accession No. BE784612. (2000).
GenBank Report for Accession No. BF035901. (2000).
GenBank Report for Accession No. BF216662. (2000).
GenBank Report for Accession No. BF680249. (2000).
GenBank Report for Accession No. P28737, Direct Submission on Dec. 1, 1992.
GenBank Report for Accession No. P54815, Direct Submission in Feb. 1996.
GenBank Report for Accession No. Z99759, Direct Submission on Aug. 1, 1996.
Kawai, et al., "Functional Annotation for a Full–Length Mouse cDNA Collection," Nature, 2001, pp. 685–690, vol. 409, The RIKEN Genome Exploration Research Group Phase II Team and the FANTOM Consortium, Macmillan Magazines, USA.
EMBL Database Report for Accession No. AA304993, Apr. 18, 1997 (XP002176450).
EMBL Database Report for Accession No. AL133327, Dec. 3, 1999 (XP002176451).
EMBL Database Report for Accession No. AK014967, Feb. 8, 2001 (XP022176452).
Notification of Transmittal of the International Search Report mailed Sep. 11, 2001 (for International Application No. PCT/US01/05597 filed Feb. 22, 2001).

* cited by examiner

Primary Examiner—Charles L. Patterson, Jr.
(74) Attorney, Agent, or Firm—Alston & Bird LLP

(57) ABSTRACT

Novel ATPase-like polypeptides, proteins, and nucleic acid molecules are disclosed. In addition to isolated, full-length ATPase-like proteins, the invention further provides isolated ATPase-like fusion proteins, antigenic peptides, and anti-ATPase-like antibodies. The invention also provides ATPase-like nucleic acid molecules, recombinant expression vectors containing a nucleic acid molecule of the invention, host cells into which the expression vectors have been introduced, and nonhuman transgenic animals in which an ATPase-like gene has been introduced or disrupted. Diagnostic, screening, and therapeutic methods utilizing compositions of the invention are also provided.

16 Claims, 14 Drawing Sheets

Parsed for domains:
```
Model          Domain    seq-f  seq-t   hmm-f  hmm-t    score   E-value
--------       ------    -----  -----   -----  -----    -----   -------
AAA             1/1       128    312..     1    220 []  244.2   1.8e-69
```

AAA: domain 1 of 1, from 128 to 312: score 244.2, E = 1.8e-69

```
               *->GvLLyGPPGTGKTlLAkAvAnelgslrkapFisisGyselvskyvGe
                  GvLLyGPPG+GKTl+AkA A+e+g    + Fi ++  s+l +k++Ge
      7970 128    GVLLYGPPGCGKTLIAKATAKEAG----CRFINLQP-STLTDKWYGE 169 sekrvRalFelArelrkraaPcpIIFiDEIDaiapkRg...gevsrrvvn
                  s k+  a+F+lA +l    +P+ IIFiDEID+ ++R+++++e ++ +++
      7970 170    SQKLAAAVFSLAIKL----QPS-IIFIDEIDSFLRNRSssdHEATAMMKA 214 qLLtemDleraGfsknssrgedtidlsnVlviaATNrpdtlDpALlRpGR
                  q++++++D    G++ +         +   +V+v++ATNrp++lD+A++R  R
      7970 215    QFMSLWD----GLDTDH--------SCQVIVMGATNRPQDLDSAIMR--R 250 fDreieiplppdeegRldIlkihlkkmplssslkqselaedvdldelaee
                  +++i  +p   +++R  +Ilk  lk+ +++           vdl  e
      7970 251    MPTRFHINQP-ALKQREAILKLILKNENVD---------RHVDLLE---- 286 iatrtegfsGADLkalcreAalrair<-*
                  +a+ t+gfsG+DLk+ cr+Aal+++r
      7970 287    VAQETDGFSGSDLKEMCRDAALLCVR       312
```

FIG. 2.

FIG. 4A. Phase 1.2.2 Expression of Gene 7970.1 w/ β2

FIG. 4B.

| Lung/ normal tumor | Lung/ Lung/ COPD | Spleen/ normal | Tonsil/ normal | Lymph node/ normal | Thymus/ normal | Epithe lial Cells (prost) | Epithe lial Cells (aortic) | Skeletal Muscle | Fibrob lasts (Dermal) | Skin/ normal | Adipo se/ Normal | Osteo blasts (prima ry) | Osteo blasts (Undiff) | Osteo blasts (Diff) | Osteo clasts | Aortic SMC Early | Aortic SMC Late | shear/ HUVEC | static HUVEC | Osteo clasts (Undiff) |
|---|---|---|---|---|---|---|---|---|---|---|---|---|---|---|---|---|---|---|---|---|
| 29.37 | 29.07 | 33.92 | 30.19 | 30.04 | 29.21 | 27.83 | 32.09 | 30.67 | 30.20 | 32.13 | 31.77 | 30.72 | 29.71 | 28.80 | 30.41 | 29.18 | 31.24 | 29.49 | 29.64 | 30.57 |
| 18.94 | 19.33 | 21.49 | 18.72 | 19.60 | 20.33 | 21.52 | 21.94 | 21.37 | 20.10 | 21.76 | 19.79 | 21.13 | 20.02 | 19.03 | 18.41 | 21.25 | 23.61 | 21.40 | 21.83 | 17.42 |
| 10.43 | 9.74 | 12.43 | 11.47 | 10.44 | 8.88 | 6.31 | 10.16 | 9.30 | 10.10 | 10.38 | 11.98 | 9.59 | 9.59 | 9.78 | 12.00 | 7.94 | 7.64 | 8.10 | 7.81 | 13.16 |
| 0.72 | 1.17 | 0.18 | 0.35 | 0.72 | 2.12 | 12.60 | 0.88 | 1.59 | 0.91 | 0.75 | 0.25 | 1.30 | 1.21 | 1.14 | 0.24 | 4.09 | 5.03 | 3.66 | 4.45 | 0.11 |

FROM FIG. 4A.

FROM FIG. 6A.

7970, A NOVEL ATPASE-LIKE MOLECULE AND USES THEREOF

CROSS-REFERENCE TO RELATED APPLICATION

This application claims the benefit of U.S. Provisional Application Ser. No. 60/185,609 filed Feb. 29, 2000, which is hereby incorporated herein in its entirety by reference.

FIELD OF THE INVENTION

The invention relates to novel ATPase-like nucleic acid sequences and proteins. Also provided are vectors, host cells, and recombinant methods for making and using the novel molecules.

BACKGROUND OF THE INVENTION

Enzymes that bind to and hydrolyze ATP play a pivotal role in translating chemically stored energy into biological activity. ATPases can function in a variety of cellular processes including, selective ion transport events, actin-based motility, membrane traffic and numerous biosynthetic pathways. Multiple ATPase families exist, including ion pumps, DEAD box-helicases, ABC transporters, and AAA (ATPases Associated to a variety of cellular Activities).

AAA proteins play essential roles in cellular housekeeping, cell division and differentiation and have been identified in prokaryotes and eukaryotes. All members of the AAA family are $Mg^{2+}$ dependent ATPases and comprise a conserved region that binds ATP. Cytosolic, transmembrane, as well as, membrane-associated AAA family members have been identified in various cellular locations and multimeric states.

The biological role of the AAA family members in the cell is diverse. Currently, members of this ATPase family are known to be involved in organelle biogenesis, cell-cycle regulation, vesicle-mediated transport, assembly of proteins through membranes, peroxisome biogenesis, gene expression in yeast and in human, and 26S proteasome function. For are view, see, Confalonieri et al. (1995) BioEssays 17:639–650.

The SEC18 gene product from *S. cerevisiae* is an AAA family member that influences the transport of proteins between the endoplasmic reticulum and the golgi complex. It has been shown that SEC18 is an essential component of a multisubunit 20S "fusion machine" that promotes membrane bilayer fusion coupled to ATP hydrolysis. The 20S fusion machine has been proposed to be involved in the assembly, fusion or division of a variety of other membrane-bound subcellular compartments such as vacuoles, nuclei, mitochondria, orperoxisomes (Wilson et al. (1992) *J. Cell. Bio*. 117:531–538). Other AAA family members are involved in mitochondrial function. YME1 is a putative ATP and zinc-dependent protease. Its inactivation leads to several morphological and functional defects, such as the escape of DNA from mitochondria (Thorsness et al. (1993) *Mol Cell Biol* 13: 5418–5426).

MSP1 is another AAA ATPase protein family member from yeast that influences mitochondrial function. MSP1 is an intrinsic mitochondrial outer membrane protein with an apparent molecular mass of 40 KDa. MSP1 is known to influence intramitochondrial protein sorting. Nakai et al. have demonstrated that the 61 mCl fusion protein, normally localized to the outer mitochondrial membrane, is mislocalized to the inner membrane of the mitochondria upon overexpression of MSP1 in yeast cell (Nakai et al. (1993) *J. Biol. Chem*. 268:24262–9).

Several members of the AAA family are involved in the biogenesis of peroxisomes. These organelles contain enzymes responsible for fatty acid oxidation and the elimination of peroxides. AAA family members, such as the PAS genes of *S. cerevisiae*, appear to be required for peroxisome growth, and proliferation (Subramani et al. (1993) *Annu. Rev. Cell Biol*. 9:445–478). Furthermore, mutations in the AAA proteins Pex1p or Pex6p accumulate abnormal peroxisomal vesicles, suggesting a defect in vesicle fusion during peroxisome assembly (Song et al. (1993) *J. Cell Biol*. 123:535–548 and Heyman et al. (1994) *J. Cell Biol*. 127:1269–1273).

AAA family members are also known to regulate transcription. Nelbock et al. described the TBP1 protein that binds human HIV TAT transactivator, thus impairing its activity in cotransfection experiments (Nelbock et al. (1990) *Science* 248: 1650–1653). TBP1 has since been identified as an AAA family member which acts as a transcriptional activator for various promoters (Ohana et al. (1993) *Proc. Natl. Acad. Scie*. 90:138–142).

Various ATP-dependent protease, such as the regulatory components Lon and Clp, are also members of the AAA ATPase family. Evidence suggests the Lon and Clp proteases are involved in DNA replication, recombination and restriction. For instance, human Lon binds specifically to single-stranded DNA in a region of the mitochondrial genome involved in regulation of DNA replication and transcription. It has been suggested that Lon may target and remodel specific DNA binding proteins either for selective degradation or for assembly (Fu et al. (1998) *Biochemistry* 37:1905–1909).

Dubiel et al. discovered that subunit 4 of the human proteasome was in fact a member of the AAA family (Dubiel et al. (1992) *J. Biol. Chem*. 267:22699–22702). Subsequently, at least 5 of the 26S-proteasome subunits already described as transcription factors or cell cycle proteins have now been identified as representatives of the AAA family. Therefore, members of the family are likely to play an essential role in ATP-dependent and ubiquitin-dependent degradation of abnormal proteins and short-lived regulatory proteins and in antigen processing.

Macromolecular machines (protein complexes) carry out nearly every major process in a cell with highly coordinated moving parts driven by energy dependent conformational changes. Examples of such structures include the proteasomes, spliceosomes, ribosomes, peroxisomes and chromosomal replicases. The intricacy of these machines require additional devices to assist in their assembly. The AAA family of ATPase is thought of as a class of molecular chaperones that assist in the noncovalent assembly of other proteins or protein complexes. Thus, the AAA family members play critical regulatory roles in the assembly or regulation of various molecular machines associated with diverse cellular activities. Accordingly, it is valuable to the field of pharmaceutical development to identify and characterize novel ATPases. The present invention advances the state of the art by providing a novel human ATPase-like nucleic acid and polypeptide.

SUMMARY OF THE INVENTION

Isolated nucleic acid molecules corresponding to ATPase-like nucleic acid sequences are provided. Additionally, amino acid sequences corresponding to the polynucleotides are encompassed. In particular, the present invention provides for isolated nucleic acid molecules comprising nucleotide sequences encoding the amino acid sequences shown in SEQ ID NO:2. Further provided are ATPase-like polypeptides having an amino acid sequence encoded by a nucleic acid molecule described herein.

The present invention also provides vectors and host cells for recombinant expression of the nucleic acid molecules described herein, as well as methods of making such vectors and host cells and for using them for production of the polypeptides or peptides of the invention by recombinant techniques.

The ATPase molecules of the present invention are useful for modulating agents in a variety of cellular processes including organelle biogenesis, cell-cycle regulation, vesicle-mediated transport, assembly of proteins through membranes, peroxisome biogenesis, protein sorting, gene expression, and 26S proteasome function. The molecules are also useful for the diagnosis and treatment of a variety of clinical conditions.

Accordingly, in one aspect, this invention provides isolated nucleic acid molecules encoding ATPase-like proteins or biologically active portions thereof, as well as nucleic acid fragments suitable as primers or hybridization probes for the detection of ATPase-like-encoding nucleic acids.

Another aspect of this invention features isolated or recombinant ATPase-like proteins and polypeptides. Preferred ATPase-like proteins and polypeptides possess at least one biological activity possessed by naturally occurring ATPase proteins.

Variant nucleic acid molecules and polypeptides substantially homologous to the nucleotide and amino acid sequences set forth in the sequence listings are encompassed by the present invention. Additionally, fragments and substantially homologous fragments of the nucleotide and amino acid sequences are provided.

Antibodies and antibody fragments that selectively bind the ATPase-like polypeptides and fragments are provided. Such antibodies are useful in detecting the ATPase-like polypeptides as well as in regulating the cellular activities influenced by the ATPase-like polypeptide.

In another aspect, the present invention provides a method for detecting the presence of ATPase-like activity or expression in a biological sample by contacting the biological sample with an agent capable of detecting an indicator of ATPase-like activity such that the presence of ATPase-like activity is detected in the biological sample.

In yet another aspect, the invention provides a method for modulating ATPase-like activity comprising contacting a cell with an agent that modulates (inhibits or stimulates) ATPase-like activity or expression such that ATPase-like activity or expression in the cell is modulated. In one embodiment, the agent is an antibody that specifically binds to ATPase-like proteins. In another embodiment, the agent modulates expression of ATPase-like protein by modulating transcription of an ATPase-like gene, splicing of an ATPase-like mRNA, or translation of an ATPase-like mRNA. In yet another embodiment, the agent is a nucleic acid molecule having a nucleotide sequence that is antisense to the coding strand of the ATPase-like mRNA or the ATPase-like gene.

In one embodiment, the methods of the present invention are used to treat a subject having a disorder characterized by aberrant ATPase-like protein activity or nucleic acid expression by administering an agent that is an ATPase-like modulator to the subject. In one embodiment, the ATPase-like modulator is an ATPase-like protein. In another embodiment, the ATPase-like modulator is an ATPase-like nucleic acid molecule. In other embodiments, the ATPase-like modulator is a peptide, peptidomimetic, or other small molecule.

The present invention also provides a diagnostic assay for identifying the presence or absence of a genetic lesion or mutation characterized by at least one of the following: (1) aberrant modification or mutation of a gene encoding an ATPase-like protein, (2) misregulation of a gene encoding an ATPase-like protein; and (3) aberrant post-translational modification of an ATPase-like protein, wherein a wild-type form of the gene encodes a protein with an ATPase-like activity.

In another aspect, the invention provides a method for identifying a compound that binds to or modulates the activity of an ATPase-like protein. In general, such methods entail measuring a biological activity of an ATPase-like protein in the presence and absence of a test compound and identifying those compounds that alter the activity of the ATPase-like protein.

The invention also features methods for identifying a compound that modulates the expression of ATPase-like genes by measuring the expression of the ATPase-like sequences in the presence and absence of the compound.

Other features and advantages of the invention will be apparent from the following detailed description and claims.

BRIEF DESCRIPTION OF THE DRAWINGS

FIG. 2 depicts an alignment of the AAA (ATPases Associated to a variety of cellular Activities) domain of the human ATPase-like sequence of the invention with a consensus amino acid sequence derived from a hidden Markov model. The upper sequence is the consensus amino acid sequence (SEQ ID NO:4), while the lower amino acid sequence corresponds to amino acids 128 to 312 of SEQ ID NO:2.

DETAILED DESCRIPTION OF THE INVENTION

Figure 1:
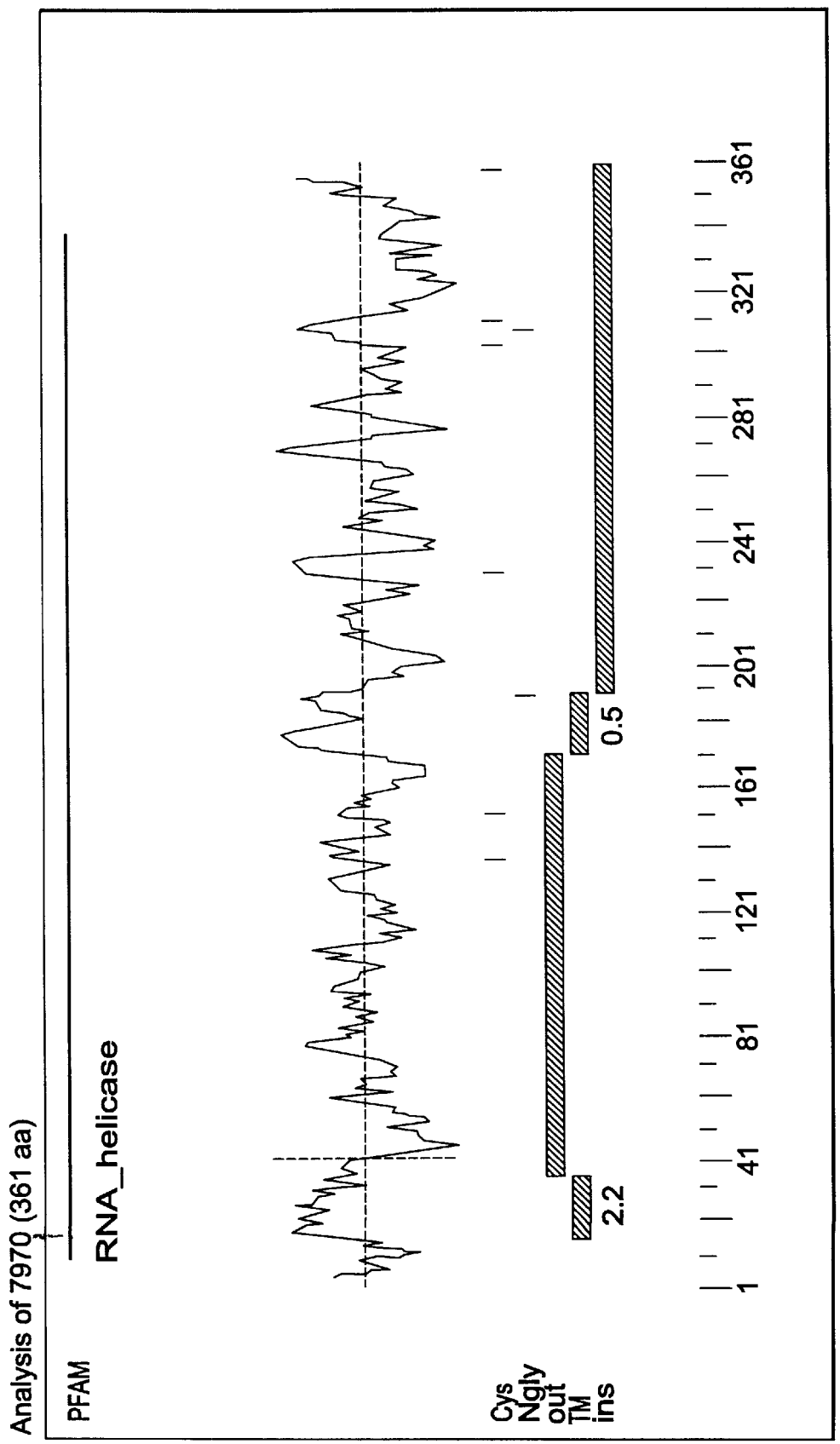
FIG. 1 depicts a hydropathy plot of a human ATPase-like molecule. Relative hydrophobic residues are shown above the dashed horizontal line, and relative hydrophilic residues are below the dashed horizontal line. The cysteine residues (cys) and N glycosylation site (Ngly) are indicated by short vertical lines just below the hydropathy trace. The numbers corresponding to the amino acid sequence (shown in SEQ ID NO:2) of human ATPase-like sequence are indicated. Polypeptides of the invention include fragments which include: all or a part of a hydrophobic sequence (a sequence above the dashed line); or all or part of a hydrophilic fragment (a sequence below the dashed line). Other fragments include a cysteine residue or as N-glycosylation site.

The present invention provides ATPase-like molecules. By "ATPase-like molecules" is intended a novel human sequence referred to as 7970, and variants and fragments thereof These full-length gene sequences or fragments thereof are referred to as "ATPase-like" sequences, indicating they share sequence similarity with ATPase genes. Isolated nucleic acid molecules comprising nucleotide sequences encoding the 7970 polypeptide whose amino acid sequence is given in SEQ ID NO:2, or a variant or fragment thereof, are provided. A nucleotide sequence encoding the 7970 polypeptide is set forth in SEQ ID NO:1 and 3. The sequences are members of the secretin family of ATPases.

A novel human ATPase-like gene sequence, referred to as 7970, is provided. This gene sequence and variants and fragments thereof are encompassed by the term "ATPase-like" molecules or sequences as used herein. The ATPase-like sequences find use in modulating a ATPase function. By "modulating" is intended the upregulating or downregulating of a response. The sequences of the invention find use in modulating organelle biogenesis, cell-cycle regulation, protein degradation, vesicle-mediated transport, assembly of proteins through membranes, peroxisome biogenesis, gene expression, and 26S proteasome function response. That is, the compositions of the invention, affect the targeted activity in either a positive or negative fashion.

Proteins and/or antibodies of the invention are also useful in modulating the above mentioned cellular process.

The present invention provides isolated nucleic acid molecules comprising nucleotide sequences encoding the ATPase-like polypeptides whose amino acid sequences are given in SEQ ID NO:2, or a variant or fragment of the polypeptides. Nucleotide sequences encoding the ATPase-like polypeptides of the invention are set forth in SEQ ID NO:1 and 3.

The disclosed invention relates to methods and compositions for the modulation, diagnosis, and treatment of a variety of disorders. Disorders involving the spleen include, but are not limited to, splenomegaly, including nonspecific acute splenitis, congestive spenomegaly, and spenic infarcts; neoplasms, congenital anomalies, and rupture. Disorders associated with splenomegaly include infections, such as nonspecific splenitis, infectious mononucleosis, tuberculosis, typhoid fever, brucellosis, cytomegalovirus, syphilis, malaria, histoplasmosis, toxoplasmosis, kala-azar, trypanosomiasis, schistosomiasis, leishmaniasis, and echinococcosis; congestive states related to partial hypertension, such as cirrhosis of the liver, portal or splenic vein thrombosis, and cardiac failure; lymphohematogenous disorders, such as Hodgkin disease, non-Hodgkin lymphomas/leukemia, multiple myeloma, myeloproliferative disorders, hemolytic anemias, and thrombocytopenic purpura; immunologic-inflammatory conditions, such as rheumatoid arthritis and systemic lupus erythematosus; storage diseases such as Gaucher disease, Niemann-Pick disease, and mucopolysaccharidoses; and other conditions, such as amyloidosis, primary neoplasms and cysts, and secondary neoplasms.

Disorders involving the lung include, but are not limited to, congenital anomalies; atelectasis; diseases of vascular origin, such as pulmonary congestion and edema, including hemodynamic pulmonary edema and edema caused by microvascular injury, adult respiratory distress syndrome (diffuse alveolar damage), pulmonary embolism, hemorrhage, and infarction, and pulmonary hypertension and vascular sclerosis; chronic obstructive pulmonary disease, such as emphysema, chronic bronchitis, bronchial asthma, and bronchiectasis; diffuse interstitial (infiltrative, restrictive) diseases, such as pneumoconioses, sarcoidosis, idiopathic pulmonary fibrosis, desquamative interstitial pneumonitis, hypersensitivity pneumonitis, pulmonary eosinophilia (pulmonary infiltration with eosinophilia), *Bronchiolitis obliterans*-organizing pneumonia, diffuse pulmonary hemorrhage syndromes, including Goodpasture syndrome, idiopathic pulmonary hemosiderosis and other hemorrhagic syndromes, pulmonary involvement in collagen vascular disorders, and pulmonary alveolar proteinosis; complications of therapies, such as drug-induced lung disease, radiation-induced lung disease, and lung transplantation; tumors, such as bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Disorders involving the colon include, but are not limited to, congenital anomalies, such as atresia and stenosis, Meckel diverticulum, congenital aganglionic megacolon-Hirschsprung disease; enterocolitis, such as diarrhea and dysentery, infectious enterocolitis, including viral gastroenteritis, bacterial enterocolitis, necrotizing enterocolitis, antibiotic-associated colitis (pseudomembranous colitis), and collagenous and lymphocytic colitis, miscellaneous intestinal inflammatory disorders, including parasites and protozoa, acquired immunodeficiency syndrome, transplantation, drug-induced intestinal injury, radiation enterocolitis, neutropenic colitis (typhlitis), and diversion colitis; idiopathic inflammatory bowel disease, such as Crohn disease and ulcerative colitis; tumors of the colon, such as non-neoplastic polyps, adenomas, familial syndromes, colorectal carcinogenesis, colorectal carcinoma, and carcinoid tumors.

Disorders involving the liver include, but are not limited to, hepatic injury; jaundice and cholestasis, such as bilirubin and bile formation; hepatic failure and cirrhosis, such as cirrhosis, portal hypertension, including ascites, portosysternic shunts, and splenomegaly; infectious disorders, such as viral hepatitis, including hepatitis A–E infection and infection by other hepatitis viruses, clinicopathologic syndromes, such as the carrier state, asymptomatic infection, acute viral hepatitis, chronic viral hepatitis, and fulminant hepatitis; autoimmune hepatitis; drug- and toxin-induced liver disease, such as alcoholic liver disease; inborn errors of metabolism and pediatric liver disease, such as hemochromatosis, Wilson disease, $\alpha_l$-antitrypsin deficiency, and neonatal hepatitis; intrahepatic biliary tract disease, such as secondary biliary cirrhosis, primary biliary cirrhosis, primary sclerosing cholangitis, and anomalies of the biliary tree; circulatory disorders, such as impaired blood flow into the liver, including hepatic artery compromise and portal vein obstruction and thrombosis, impaired blood flow through the liver, including passive congestion and centrilobular necrosis and peliosis hepatis, hepatic vein outflow obstruction, including hepatic vein thrombosis (Budd-Chiari syndrome) and veno-occlusive disease; hepatic disease associated with pregnancy, such as preeclampsia and eclarmpsia, acute fatty liver of pregnancy, and intrehepatic cholestasis of pregnancy; hepatic complications of organ or bone marrow transplantation, such as drug toxicity after bone marrow transplantation, graft-versus-host disease and liver rejection, and nonimmunologic damage to liver allografts; tumors and tumorous conditions, such as nodular hyperplasias, adenomas, and malignant tumors, including primary carcinoma of the liver and metastatic tumors.

Disorders involving the uterus and endometrium include, but are not limited to, endometrial histology in the menstrual cycle; functional endometrial disorders, such as anovulatory cycle, inadequate luteal phase, oral contraceptives and induced endometrial changes, and menopausal and postmenopausal changes; inflammations, such as chronic endometritis; adenomyosis; endometriosis; endometrial polyps; endometrial hyperplasia; malignant tumors, such as carcinoma of the endometrium; mixed Muillerian and mesenchymal tumors, such as malignant mixed Müllerian tumors; tumors of the myometrium, including leiomyomas, leiomyosarcomas, and endometrial stromal tumors.

Disorders involving the brain include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured beny aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-bome (Arbo) viral encephalitis, *Herpes simplex* virus Type 1, *Herpes simplex* virus Type 2, *Varicalla-zoster* virus (*Herpes zoster*), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degeneration, multiple system atrophy, including striatonigral degeneration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

Disorders involving T-cells include, but are not limited to, cell-mediated hypersensitivity, such as delayed type hypersensitivity and T-cell-mediated cytotoxicity, and transplant rejection; autoimmune diseases, such as systemic lupus erythematosus, Sjogren syndrome, systemic sclerosis, inflammatory myopathies, mixed connective tissue disease, and polyarteritis nodosa and other vasculitides; immunologic deficiency syndromes, including but not limited to, primary immunodeficiencies, such as thymic hypoplasia, severe combined immunodeficiency diseases, and AIDS; leukopenia; reactive (inflammatory) proliferations of white cells, including but not limited to, leukocytosis, acute nonspecific lymphadenitis, and chronic nonspecific lymphadenitis; neoplastic proliferations of white cells, including but not limited to lymphoid neoplasms, such as precursor T-cell neoplasms, such as acute lymphoblastic leukemia/lymphoma, peripheral T-cell and natural killer cell neoplasms that include peripheral T-cell lymphoma, unspecified, adult T-cell leukemia/lymphoma, mycosis fungoides and Sezary syndrome, and Hodgkin disease.

Diseases of the skin, include but are not limited to, disorders of pigmentation and melanocytes, including but not limited to, vitiligo, freckle, melasma, lentigo, nevocellular nevus, dysplastic nevi, and malignant melanoma; benign epithelial tumors, including but not limited to, seborrheic keratoses, acanthosis nigricans, fibroepithelial polyp, epithelial cyst, keratoacanthoma, and adnexal (appendage) tumors; premalignant and malignant epidermal tumors, including but not limited to, actinic keratosis, squamous cell carcinoma, basal cell carcinoma, and merkel cell carcinoma; tumors of the dermis, including but not limited to, benign fibrous histiocytoma, dermatofibrosarcoma protuberans, xanthomas, and dermal vascular tumors;

tumors of cellular immigrants to the skin, including but not limited to, histiocytosis X, mycosis fungoides (cutaneous T-cell lymphoma), and mastocytosis; disorders of epidermal maturation, including but not limited to, ichthyosis; acute inflammatory dermatoses, including but not limited to, urticaria, acute eczematous dermatitis, and erythema multiforme; chronic inflammatory dermatoses, including but not limited to, psoriasis, lichen planus, and lupus erythematosus; blistering (bullous) diseases, including but not limited to, pemphigus, bullous pemphigoid, dermatitis herpetiformis, and noninflammatory blistering diseases: epidermolysis bullosa and porphyria; disorders of epidermal appendages, including but not limited to, acne vulgaris; panniculitis, including but not limited to, erythema nodosum and erythema induratum; and infection and infestation, such as verrucae, molluscum contagiosum, impetigo, superficial fungal infections, and arthropod bites, stings, and infestations.

In normal bone marrow, the myelocytic series (polymorphoneuclear cells) make up approximately 60% of the cellular elements, and the erythrocytic series, 20–30%. Lymphocytes, monocytes, reticular cells, plasma cells and megakaryocytes together constitute 10–20%. Lymphocytes make up 5–15% of normal adult marrow. In the bone marrow, cell types are add mixed so that precursors of red blood cells (erythroblasts), macrophages (monoblasts), platelets (megakaryocytes), polymorphoneuclear leucocytes (myeloblasts), and lymphocytes (lymphoblasts) can be visible in one microscopic field. In addition, stem cells exist for the different cell lineages, as well as a precursor stem cell for the committed progenitor cells of the different lineages. The various types of cells and stages of each would be known to the person of ordinary skill in the art and are found, for example, on page 42 (FIGS. 2–8) of *Immunology, Imunopathology and Immunity*, Fifth Edition, Sell et al. Simon and Schuster (1996), incorporated by reference for its teaching of cell types found in the bone marrow. According, the invention is directed to disorders arising from these cells. These disorders include but are not limited to the following: diseases involving hematopoeitic stem cells; committed lymphoid progenitor cells; lymphoid cells including B and T-cells; committed myeloid progenitors, including monocytes, granulocytes, and megakaryocytes; and committed erythroid progenitors. These include but are not limited to the leukemias, including B-lymphoid leukemias, T-lymphoid leukemias, undifferentiated leukemias; erythroleukemia, megakaryoblastic leukemia, monocytic; [leukemias are encompassed with and without differentiation; chronic and acute lymphoblastic leukemia, chronic and acute lymphocytic leukemia, chronic and acute myelogenous leukemia, lymphoma, myelo dysplastic syndrome, chronic and acute myeloid leukemia, myelomonocytic leukemia; chronic and acute myeloblastic leukemia, chronic and acute myelogenous leukemia, chronic and acute promyelocytic leukemia, chronic and acute myelocytic leukemia, hematologic malignancies of monocyte-macrophage lineage, such as juvenile chronic myelogenous leukemia; secondary AML, antecedent hematological disorder, refractory anemia; aplastic anemia; reactive cutaneous angioendotheliomatosis; fibrosing disorders involving altered expression in dendritic cells, disorders including systemic sclerosis, E–M syndrome, epidemic toxic oil syndrome, eosinophilic fasciitis localized forms of scleroderma, keloid, and fibrosing colonopathy; angiomatoid malignant fibrous histiocytoma; carcinoma, including primary head and neck squamous cell carcinoma; sarcoma, including kaposi's sarcoma; fibroadanoma and phyllodes tumors, including mammary fibroadenoma; stromal tumors; phyllodes tumors, including histiocytoma; erythroblastosis; neurofibromatosis; diseases of the vascular endothelium; demyelinating, particularly in old lesions; gliosis, vasogenic edema, vascular disease, Alzheimer's and Parkinson's disease; T-cell lymphomas; B-cell lymphomas.

Disorders involving the heart, include but are not limited to, heart failure, including but not limited to, cardiac hypertrophy, left-sided heart failure, and right-sided heart failure; ischemic heart disease, including but not limited to angina pectoris, myocardial infarction, chronic ischemic heart disease, and sudden cardiac death; hypertensive heart disease, including but not limited to, systemic (left-sided) hypertensive heart disease and pulmonary (right-sided) hypertensive heart disease; valvular heart disease, including but not limited to, valvular degeneration caused by calcification, such as calcific aortic stenosis, calcification of a congenitally bicuspid aortic valve, and mitral annular calcification, and myxomatous degeneration of the mitral valve (mitral valve prolapse), rheumatic fever and rheumatic heart disease, infective endocarditis, and noninfected vegetations, such as nonbacterial thrombotic endocarditis and endocarditis of systemic lupus erythematosus (Libman-Sacks disease), carcinoid heart disease, and complications of artificial valves; myocardial disease, including but not limited to dilated cardiomyopathy, hypertrophic cardiomyopathy, restrictive cardiomyopathy, and myocarditis; pericardial disease, including but not limited to, pericardial effusion and hemopericardium and pericarditis, including acute pericarditis and healed pericarditis, and rheumatoid heart disease; neoplastic heart disease, including but not limited to, primary cardiac tumors, such as myxoma, lipoma, papillary fibroelastoma, rhabdomyoma, and sarcoma, and cardiac effects of noncardiac neoplasms; congenital heart disease, including but not limited to, left-to-right shunts—late cyanosis, such as atrial septal defect, ventricular septal defect, patent ductus arteriosus, and atrio-ventricular septal defect, right-o-left shunts—early cyanosis, such as tetralogy of fallot, transposition of great arteries, truncus arteriosus, tricuspid atresia, and total anomalous pulmonary venous connection, obstructive congenital anomalies, such as coarctation of aorta, pulmonary stenosis and atresia, and aortic stenosis and atresia, and disorders involving cardiac transplantation.

Disorders involving blood vessels include, but are not limited to, responses of vascular cell walls to injury, such as endothelial dysfunction and endothelial activation and intimal thickening, vascular diseases including, but not limited to, congenital anomalies, such as arteriovenous fistula, atherosclerosis, and hypertensive vascular disease, such as hypertension; inflammatory disease—the vasculitides, such as giant cell (temporal) arteritis, Takayasu arteritis, polyarteritis nodosa (classic), Kawasaki syndrome (mucocutaneous lymph node syndrome), microscopic polyanglitis (microscopic polyarteritis, hypersensitivity or leukocytoclastic anglitis), Wegener granulomatosis, thromboanglitis obliterans (Buerger disease), vasculitis associated with other disorders, and infectious arteritis; Raynaud disease; aneurysms and dissection, such as abdominal aortic aneurysms, syphilitic (luetic) aneurysms, and aortic dissection (dissecting hematoma); disorders of veins and lymphatics, such as varicose veins, thrombophlebitis and phlebothrombosis, obstruction of superior vena cava (superior vena cava syndrome), obstruction of inferior vena cava (inferior vena cava syndrome), and lymphangitis and lymphedema, tumors, including benign tumors and tumor-like conditions, such as hemangioma, lymphangioma, glomus tumor (glomangioma), vascular ectasias, and bacillary angiomatosis, and intermediate-grade (borderline low-grade malignant) tumors, such as Kaposi sarcoma and hemangloendothelioma, and malignant tumors, such as angiosarcoma and hemangiopericytoma; and pathology of therapeutic interventions in vascular disease, such as balloon angioplasty and related techniques and vascular replacement, such as coronary artery bypass graft surgery.

Disorders involving red cells include, but are not limited to, anemias, such as hemolytic anemias, including hereditary spherocytosis, hemolytic disease due to erythrocyte enzyme defects: glucose-6-phosphate dehydrogenase deficiency, sickle cell disease, thalassemia syndromes, paroxysmal nocturnal hemoglobinuria, immunohemolytic anemia, and hemolytic anemia resulting from trauma to red cells; and anemias of diminished erythropoiesis, including megaloblastic anemias, such as anemias of vitamin B12 deficiency: pernicious anemia, and anemia of folate deficiency, iron deficiency anemia, anemia of chronic disease, aplastic anemia, pure red cell aplasia, and other forms of marrow failure.

Disorders involving the thymus include developmental disorders, such as DiGeorge syndrome with thymic hypoplasia or aplasia; thymic cysts; thymic hypoplasia, which involves the appearance of lymphoid follicles within the thymus, creating thymic follicular hyperplasia; and thymomas, including germ cell tumors, lynphomas, Hodgkin disease, and carcinoids. Thymomas can include benign or encapsulated thymoma, and malignant thymoma Type I (invasive thymoma) or Type II, designated thymic carcinoma.

Disorders involving B-cells include, but are not limited to precursor B-cell neoplasms, such as lymphoblastic leukemia/lymphoma. Peripheral B-cell neoplasms include, but are not limited to, chronic lymphocytic leukemia/small lymphocytic lymphoma, follicular lymphoma, diffuse large B-cell lymphoma, Burkitt lymphoma, plasma cell neoplasms, multiple myeloma, and related entities, lymphoplasmacytic lymphoma (Waldenström macroglobulinemia), mantle cell lymphoma, marginal zone lymphoma (MALToma), and hairy cell leukemia.

Disorders involving the kidney include, but are not limited to, congenital anomalies including, but not limited to, cystic diseases of the kidney, that include but are not limited to, cystic renal dysplasia, autosomal dominant (adult) polycystic kidney disease, autosomal recessive (childhood) polycystic kidney disease, and cystic diseases of renal medulla, which include, but are not limited to, medullary sponge kidney, and nephronophthisis-uremic medullary cystic disease complex, acquired (dialysis-associated) cystic disease, such as simple cysts; glomerular diseases including pathologies of glomerular injury that include, but are not limited to, in situ immune complex deposition, that includes, but is not limited to, anti-GBM nephritis, Heymann nephritis, and antibodies against planted antigens, circulating immune complex nephritis, antibodies to glomerular cells, cell-mediated immunity in glomerulonephritis, activation of alternative complement pathway, epithelial cell injury, and pathologies involving mediators of glomerular injury including cellular and soluble mediators, acute glomerulonephritis, such as acute proliferative (poststreptococcal, postinfectious) glomerulonephritis, including but not limited to, poststreptococcal glomerulonephritis and nonstreptococcal acute glomerulonephritis, rapidly progressive c(crescentic) glomerulonephritis, nephrotic syndrome, membranous glomerulonephritis (membranous nephropathy), minimal change disease (lipoid nephrosis), focal segmental glomerulosclerosis, membranoproliferative glomerulonephritis, IgA nephropathy (Berger disease), focal proliferative and necrotizing glomerulonephritis (focal glomerulonephritis), hereditary nephritis, including but not limited to, Alport syndrome and thin membrane disease (benign familial hematuria), chronic glomerulonephritis, glomerular lesions associated with systemic disease, including but not limited to, systemic lupus erythematosus, Henoch-Schönlein purpura, bacterial endocarditis, diabetic glomerulosclerosis, amyloidosis, fibrillary and inmmunotactoid glomerulonephritis, and other systemic disorders; diseases affecting tubules and interstitium, including acute tubular necrosis and tubulointerstitial nephritis, including but not limited to, pyelonephritis and urinary tract infection, acute pyelonephritis, chronic pyelonephritis and reflux nephropathy, and tubulointerstitial nephritis induced by drugs and toxins, including but not limited to, acute drug-induced interstitial nephritis, analgesic abuse nephropathy, nephropathy associated with nonsteroidal anti-inflammatory drugs, and other tubulointerstitial diseases including, but not limited to, urate nephropathy, hypercalcemia and nephrocalcinosis, and multiple myeloma; diseases of blood vessels including benign nephrosclerosis, malignant hypertension and accelerated nephrosclerosis, renal artery stenosis, and thrombotic microangiopathies including, but not limited to, classic (childhood) hemolytic-uremic syndrome, adult hemolytic-uremic syndrome/thrombotic thrombocytopenic purpura, idiopathic HUS/TTP, and other vascular disorders including, but not limited to, atherosclerotic ischemic renal disease, atheroembolic renal disease, sickle cell disease nephropathy, diffuse cortical necrosis, and renal infarcts; urinary tract obstruction (obstructive uropathy); urolithiasis (renal calculi, stones); and tumors of the kidney including, but not limited to, benign tumors, such as renal papillary adenoma, renal fibroma or hamartoma (renomedullary interstitial cell tumor), angiomyolipoma, and oncocytoma, and malignant tumors, including renal cell carcinoma (hypemephroma, adenocarcinoma of kidney), which includes urothelial carcinomas of renal pelvis.

Disorders of the breast include, but are not limited to, disorders of development; inflanmmations, including but not limited to, acute mastitis, periductal mastitis, periductal mastitis (recurrent subareolar abscess, squamous metaplasia of lactiferous ducts), mammary duct ectasia, fat necrosis, granulomatous mastitis, and pathologies associated with silicone breast implants; fibrocystic changes; proliferative breast disease including, but not limited to, epithelial hyperplasia, sclerosing adenosis, and small duct papillomas; tumors including, but not limited to, stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, no special type, invasive lobular carcinoma, medullary carcinoma, colloid (mucinous) carcinoma, tubular carcinoma, and invasive papillary carcinoma, and miscellaneous malignant neoplasms.

Disorders in the male breast include, but are not limited to, gynecomastia and carcinoma.

Disorders involving the testis and epididymis include, but are not limited to, congenital anomalies such as cryptorchidism, regressive changes such as atrophy, inflammations such as nonspecific epididymitis and orchitis, granulomatous (autoimmune) orchitis, and specific inflammations including, but not limited to, gonorrhea, mumps, tuberculosis, and syphilis, vascular disturbances including torsion, testicular tumors including germ cell tumors that include, but are not limited to, seminoma, spermatocytic seminoma, embryonal carcinoma, yolk sac tumor choriocarcinoma, teratoma, and mixed tumors, tumore of sex cord-gonadal stroma including, but not limited to, Leydig (interstitial) cell tumors and sertoli cell tumors (androblastoma), and testicular lymphoma, and miscellaneous lesions of tunica vaginalis.

Disorders involving the prostate include, but are not limited to, inflammations, benign enlargement, for example, nodular hyperplasia (benign prostatic hypertrophy or hyperplasia), and tumors such as carcinoma.

Disorders involving the thyroid include, but are not limited to, hyperthyroidism; hypothyroidism including, but not limited to, cretinism and myxedema; thyroiditis including, but not limited to, hashimoto thyroiditis, subacute (granulomatous) thyroiditis, and subacute lymphocytic (painless) thyroiditis; Graves disease; diffuse and multinodular goiter including, but not limited to, diffuse nontoxic (simple) goiter and multinodular goiter, neoplasms of the thyroid including, but not limited to, adenomas, other benign tumors, and carcinomas, which include, but are not limited to, papillary carcinoma, follicular carcinoma, medullary carcinoma, and anaplastic carcinoma; and cogenital anomalies.

Disorders involving the skeletal muscle include tumors such as rhabdomyosarcoma.

Disorders involving the pancreas include those of the exocrine pancreas such as congenital anomalies, including but not limited to, ectopic pancreas; pancreatitis, including but not limited to, acute pancreatitis; cysts, including but not limited to, pseudocysts; tumors, including but not limited to, cystic tumors and carcinoma of the pancreas; and disorders of the endocrine pancreas such as, diabetes mellitus; islet cell tumors, including but not limited to, insulinomas, gastrinomas, and other rare islet cell tumors.

Disorders involving the small intestine include the malabsorption syndromes such as, celiac sprue, tropical sprue (postinfectious sprue), whipple disease, disaccharidase (lactase) deficiency, abetalipoproteinemia, and tumors of the small intestine including adenomas and adenocarcinoma.

Disorders related to reduced platelet number, thrombocytopenia, include idiopathic thrombocytopenic purpura, including acute idiopathic thrombocytopenic purpura, drug-induced thrombocytopenia, HIV-associated thrombocytopenia, and thrombotic microangiopathies: thrombotic thrombocytopenic purpura and hemolytic-uremic syndrome.

Disorders involving precursor T-cell neoplasms include precursor T lymphobl astic leukemia/lymphoma. Disorders involving peripheral T-cell and natural killer cell neoplasms include T-cell chronic lymphocytic leukemia, large granular lymphocytic leukemia, mycosis fungoides and Sézary syndrome, peripheral T-cell lymphoma, unspecified, angioimmunoblastic T-cell lymphoma, angiocentric lymphoma (NK/T-cell lymphoma[4a]), intestinal T-cell lymphoma, adult T-cell leukemia/lymphoma, and anaplastic large cell lymphoma.

Disorders involving the ovary include, for example, polycystic ovarian disease, Stein-leventhal syndrome, Pseudomyxoma peritonei and stromal hyperthecosis; ovarian tumors such as, tumors of coelomic epithelium, serous tumors, mucinous tumors, endometeriod tumors, clear cell adenocarcinoma, cystadenofibroma, brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecoma-fibromas, androblastomas, hill cell tumors, and gonadoblastoma; and metastatic tumors such as Krukenberg tumors.

Bone-forming cells include the osteoprogenitor cells, osteoblasts, and osteocytes. The disorders of the bone are complex because they may have an impact on the skeleton during any of its stages of development. Hence, the disorders may have variable manifestations and may involve one, multiple or all bones of the body. Such disorders include, congenital malformations, achondroplasia and thanatophoric dwarfism, diseases associated with abnormal matix such as type 1 collagen disease, osteoporosis, Paget disease, rickets, osteomalacia, high-tumover osteodystrophy, low-tumover of aplastic disease, osteonecrosis, pyogenic osteomyelitis, tuberculous osteomyelitism, osteoma, osteoid osteoma, osteoblastoma, osteosarcoma, osteochondroma, chondromas, chondroblastoma, chondromyxoid fibroma, chondrosarcoma, fibrous cortical defects, fibrous dysplasia, fibrosarcoma, malignant fibrous histiocytoma, Ewing sarcoma, primitive neuroectodermal tumor, giant cell tumor, and metastatic tumors.

The ATPase-like gene, clone 7970, was identified in a cDNA library. Clone 7970 encodes a mRNA transcript having the corresponding cDNA set forth in SEQ ID NO:1. This transcript has a 1086 nucleotide open reading frame (nucleotides 79–1165 of SEQ ID NO:1), which encodes a 361 amino acid protein (SEQ ID NO:2). An analysis of the full-length 7970 polypeptide predicts that the N-terminal 41 amino acids represent a signal peptide. Transmembrane segments from amino acids (aa) 16–34 and 173–191 were predicted by MEMSAT. Transmembrane segments were also predicted from aa 133–151 of the presumed mature peptide sequence. Prosite program analysis was used to predict various sites within the 7970 protein. N-glycosylation sites were predicted at aa 200–203 and 316–319. Protein kinase C phosphorylation sites were predicted at aa 33–35, 44–46, 146–148, 163–165, 170–172 and 273–239. Casein kinase II phosphorylation sites were predicted at aa 12–15, 70–73, 89–92, 146–149, 161–164, 202–205, 218–212, 295–298, 317–320, and 322–325. An N-myristoylation site is predicted at aa 136–141. An ATP/GTP-binding site motif A (P-loop) was predicted at aa 133–140. A Leucine zipper pattern was predicted at aa 109–130.

The ATPase-like protein possesses a NB-ARC domain, from aa 131–145, an AAA domain from aa 128–312, an adenylate kinase domain from aa 131–139, a RNA helicase domain from aa 7–337, as predicted by HMMer, Version 2. For general information regarding PFAM identifiers, PS prefix and PF prefix domain identification numbers, refer to Sonnhammer et al. (1997) *Protein* 28:405–420 and http//www.psc.edu/general/software/packages/pfam/pfam.html. The NB-ARC domain is a novel signaling motif shared by plant resistant gene products and regulators of cell death in animals. See for example, Van der Biezen et al. (1998) *Curr Biol* 8:229–227. Adenylate kinase is a small monomeric enzyme that catalyzes the reversible transfer of MgATP to AMP. In mammals there are three different isozymes: AK1 (or myokinase), which is cytosolic; AK2, which is located in the outer compartment of mitochondria; and, AK3 (or GTP:AMP phosphotransferase), which is located in the mitochondrial matrix and which uses MgGTP instead of MgATP. The RNA helices domain is found in a family of RNA helices thought to be involved in duplex unwinding during viral RNA replication. Members of this family are found in a variety of single stranded RNA viruses. See for example, Gorbalenya et al. (1989) *NAR* 17:4713–4730. The AAA domain (ATPase Associated with various cellular Activities) is found in a family of proteins that often perform chaperone-like functions that assist in the assembly, operation, or disassembly of protein complexes. See for example, Confalonieri et al. (1995) *Bioessays* 17:639–650 and Neuwald et al. (1999) *Genome Research* 9:27–43.

The 7970 protein displays 37% identity from aa 202–312, 34% identity from aa 154–292, and 57% identity to aa 128–165 to a Prodom consensus sequence found in members of the Lon family of ATP-dependent proteases; 25% identity from aa 13–127 to a Prodom consensus sequence found in the MSP1 protein homolog; 25% identity from aa 126–336 to a Prodom consensus sequence found in a putative cell division protein from *Treponema pallidum*; 22% identity from aa 130–347 to a Prodom consensus sequence found in a probable Peroxin-6 protein which may play a role in biogenesis of peroxisomes; 35% identity from aa 77–351 and 31% identity from aa 324–351 to a Prodom consensus sequence found in members of the peptidase family 16S; 20% identity from aa 129–355 to a Prodom consensus sequence found in a chromosomal replication initiator protein; and, 32% identity from aa 117–198 to a Prodom consensus sequence found in a TAT-binding homolog. Furthermore, the amino acid sequence of the 7970 sequence shares approximately 47% sequence identity with the *C. elegans* MSP1 protein homolog (Genbank Accession No. P54815). This sequence alignment was generated using the clustal method.

The ATPase-like sequences of the invention are members of a family of molecules (the "ATPase family") having conserved functional features. The term "family" when referring to the proteins and nucleic acid molecules of the invention is intended to mean two or more proteins or nucleic acid molecules having sufficient amino acid or nucleotide sequence identity as defined herein. Such family members can be naturally occurring and can be from either the same or different species. For example, a family can contain a first protein of murine origin and a homologue of that protein of human origin, as well as a second, distinct protein of human origin and a murine homologue of that protein. Members of a family may also have common functional characteristics.

Figure 3:
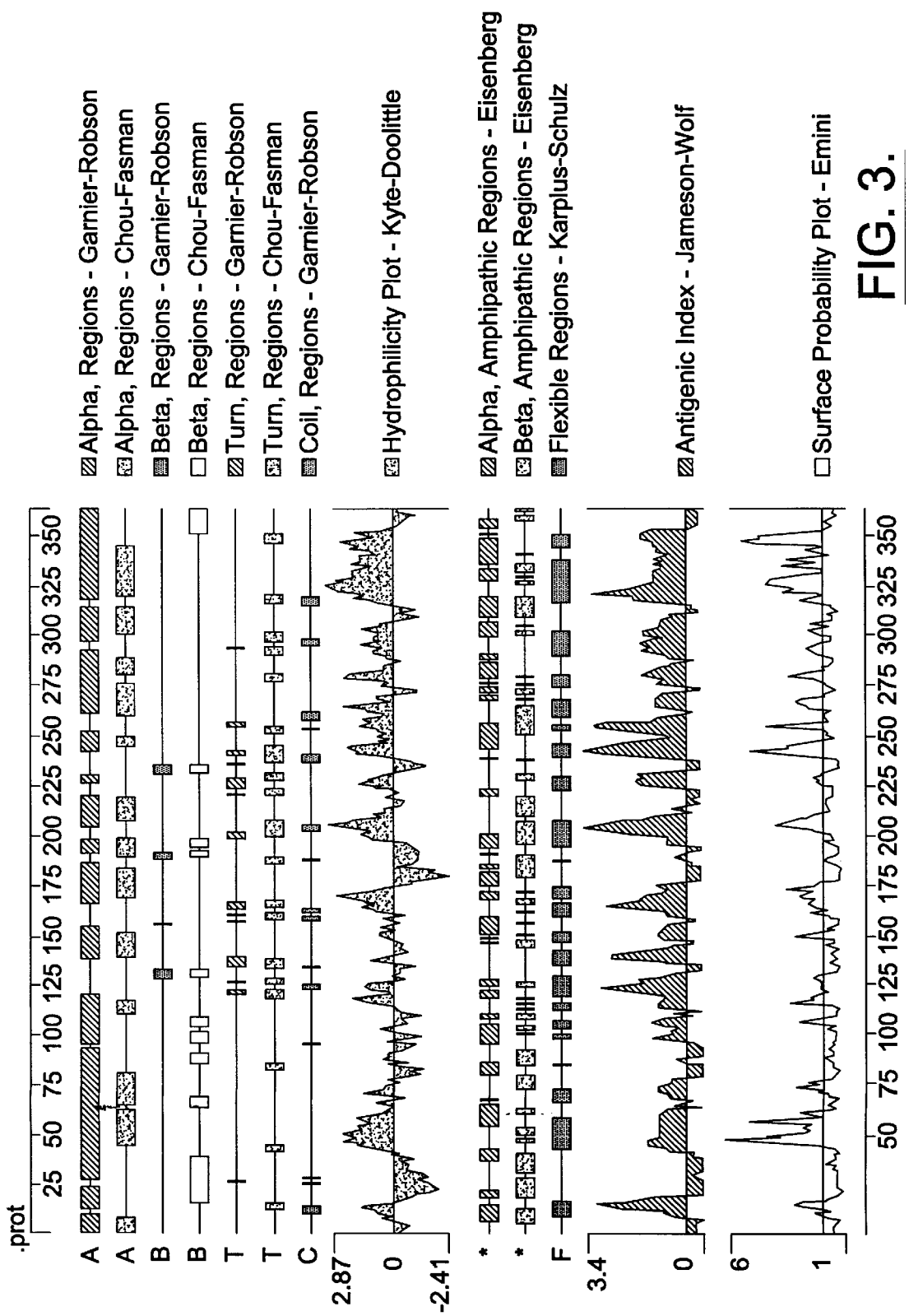
FIG. 3 shows an analysis of the 7970 amino acid sequence:αβ turn and coil regions; hydrophilicity; amphipathic regions, flexible regions; antigenic index; and surface probability plot.

As used herein, the term "AAA domain" includes an amino acid sequence of about 80–184 amino acid residues in length and having a bit score for the alignment of the sequence to the AAA domain (HMM) of at least 8. Preferably, an AAA domain includes at least about 50–200 amino acids, more preferably about 100–185 amino acid residues, or about 81–185 amino acids and has a bit score for the alignment of the sequence to the AAA domain (HMM) of at least 16 or greater. The AAA domain (BNM) has been assigned the PFAM Accession No. PF00004 (http://pfam.wustl.edu/). An alignment of the AAA domain (amino acids 128 to 312 of SEQ ID NO:2) of the human ATPase-like sequence with a consensus amino acid sequence derived from a hidden Markov model is depicted in FIG. 3.

In a preferred embodiment ATPase-like polypeptide or protein has a "AAA domain" or a region which includes at least about 100–250 more preferably about 130–200 or 160–200 amino acid residues and has at least about 60%, 70%, 80%, 90%, 95%, 99%, or 100% sequence identity with an "AAA domain," e.g., the AAA domain of human ATPase-like molecule (e.g., amino acid residues 128–312 of SEQ ID NO:2).

To identify the presence of an "AAA" domain in an ATPase-like protein sequence, and make the determination that a polypeptide or protein of interest has a particular profile, the amino acid sequence of the protein can be searched against a database of HMMs (e.g., the Pfam database, release 2.1) using the default parameters (http://www.sanger.ac.uk/Software/Pfam/HMM search). For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28(3): 405–420 and a detailed description of HMMs can be found, for example, in Gribskov et al. (1990) *Meth. Enzymol.* 183:146–159; Gribskov et al. (1987) *Proc. Natl. Acad. Sci. USA* 84:4355–4358; Krogh et al. (1994) *J. Mol. Biol.* 235:1501–1531; and Stultz et al. (1993) *Protein Sci.* 2:305–314, the contents of which are incorporated herein by reference.

In one embodiment, an ATPase-like protein includes at least one transmembrane domain. As used herein, the term "transmembrane domain" includes an amino acid sequence of about 15 amino acid residues in length that spans a phospholipid membrane. More preferably, a transmembrane domain includes about at least 18, 20, 22, 24, 25, 30, 35 or 40 amino acid residues and spans a phospholipid membrane. Transmembrane domains are rich in hydrophobic residues, and typically have an a-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, http://pfam.wustl.edu/cgi-bin/getdesc?name=7tm–1, and Zagotta W. N. et al. (1996) *Annual Rev. Neuronsci.* 19:235–63, the contents of which are incorporated herein by reference.

In a preferred embodiment, an ATPase-like polypeptide or protein has at least one transmembrane domain or a region which includes at least 18, 20, 22, 24, 25, 30, 35 or 40 amino acid residues and has at least about 60%, 70% 80% 90% 95%, 99%, or 100% sequence identity with a "transmembrane domain," e.g., at least one transmembrane domain of human ATPase-like (e.g., amino acid residues 18 of SEQ ID NO:2).

In another embodiment, an ATPase-like protein includes at least one "non-transmembrane domain." As used herein, "non-transmembrane domains" are domains that reside outside of the membrane. When referring to plasma membranes, non-transmembrane domains include extracellular domains (i.e., outside of the cell) and intracellular domains (i.e., within the cell). When referring to membrane-bound proteins found in intracellular organelles (e.g., mitochondria, endoplasmic reticulum, peroxisomes and microsomes), non-transmembrane domains include those domains of the protein that reside in the cytosol (i.e., the cytoplasm), the lumen of the organelle, or the matrix or the intermembrane space (the latter two relate specifically to mitochondria organelles). The C-terminal amino acid residue of a non-transmembrane domain is adjacent to an N-terminal amino acid residue of a transmembrane domain in a naturally occurring ATPase-like, or ATPase-like protein.

In a preferred embodiment, an ATPase-like polypeptide or protein has a "non-transmembrane domain" or a region which includes at least about 1–170, preferably about 100–170, about 50–160, and about 20–125 amino acid residues, and has at least about 60%, 70% 80% 90% 95%, 99% or 100% sequence identity with a "non-transmembrane domain", e.g., a non-transmembrane domain of human ATPase-like (e.g., residues 191 and 361 of SEQ ID NO:2). Preferably, a non-transmembrane domain is capable of catalytic activity (e.g., ATPase-like activity).

A non-transmembrane domain located at the N-terminus of an ATPase-like protein or polypeptide is referred to herein as an "N-terminal non-transmembrane domain." As used herein, an "N-terminal non-transmembrane domain" includes an amino acid sequence having about 1–350, preferably about 30–325, more preferably about 50–320, or even more preferably about 80–310 amino acid residues in length and is located outside the boundaries of a membrane. For example, an N-terminal non-transmembrane domain is located at about amino acid residues 1–15 of SEQ ID NO:2.

Similarly, a non-transmembrane domain located at the C-terminus of an ATPase-like protein or polypeptide is referred to herein as a "C-terminal non-transmembrane domain." As used herein, an "C-terminal non-transmembrane domain" includes an amino acid sequence having about 1–300, preferably about 15–290, preferably about 20–270, more preferably about 25–255 amino acid residues in length and is located outside the boundaries of a membrane. For example, an C-terminal non-transmembrane domain is located at about amino acid residues 191–361 of SEQ ID NO:2.

An ATPase-like molecule can further include a signal sequence. As used herein, a "signal sequence" refers to a peptide of about 20–80 amino acid residues in length which occurs at the N-terminus of secretory and integral membrane proteins and which contains a majority of hydrophobic amino acid residues. For example, a signal sequence contains at least about 12–25 amino acid residues, preferably about 30–70 amino acid residues, more preferably about 61 amino acid residues, and has at least about 40–70%, preferably about 50–65%, and more preferably about 55–60% hydrophobic amino acid residues (e.g., alanine, valine, leucine, isoleucine, phenylalanine, tyrosine, tryptophan, or proline). Such a "signal sequence", also referred to in the art as a "signal peptide", serves to direct a protein containing such a sequence to a lipid bilayer. For example, in one embodiment, an ATPase-like protein contains a signal sequence of about amino acids 1–41 of SEQ ID NO:2. The "signal sequence" is cleaved during processing of the mature protein. The mature ATPase-like protein corresponds to amino acids 42–361 of SEQ ID NO:2.

Preferred ATPase-like polypeptides of the present invention have an amino acid sequence sufficiently identical to the amino acid sequence of SEQ ID NO:2. The term "sufficiently identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity. For example, amino acid or nucleotide sequences that contain a common structural domain having at least about 45%, 55%, or 65% identity, preferably 75% identity, more preferably 85%, 95%, or 98% identity are defined herein as sufficiently identical.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. In a preferred embodiment, the percent identity between two amino acid sequences is determined using the Needleman and Wunsch (1970) *J. Mol. Biol.* 48:444–453 algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) is using a Blossum 62 scoring matrix with a gap open penalty of 12, a gap extend penalty of 4, and a frameshift gap penalty of 5.

The percent identity between two amino acid or nucleotide sequences can be determined using the algorithm of Karlin and Altschul (1990) *Proc. Natl. Acad. Sci. USA* 87:2264, modified as in Karlin and Altschul (1993) *Proc. Natl. Acad. Sci. USA* 90:5873–5877. Such an algorithm is incorporated into the NBLAST and XBLAST programs of Altschul et al. (1990) *J. Mol. Biol.* 215:403. BLAST nucleotide searches can be performed with the NBLAST program, score=100, wordlength=12, to obtain nucleotide sequences homologous to ATPase-like nucleic acid molecules of the invention. BLAST protein searches can be performed with the XBLAST program, score=50, wordlength=3, to obtain amino acid sequences homologous to ATPase-like protein molecules of the invention. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., XBLAST and NBLAST) can be used. See http://www.ncbi.nln.nih.gov. Another preferred, non-limiting example of a mathematical algorithm utilized for the comparison of sequences is the algorithm of Myers and Miller (1988) *CABIOS* 4:11–17. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used.

Accordingly, another embodiment of the invention features isolated ATPase-like proteins and polypeptides having an ATPase-like protein activity. As used interchangeably herein, a "ATPase-like protein activity", "biological activity of an ATPase-like protein", or "functional activity of an ATPase-like protein" refers to an activity exerted by an ATPase-like protein, polypeptide, or nucleic acid molecule on an ATPase-like responsive cell as determined in vivo, or in vitro, according to standard assay techniques. An ATPase-like activity can be a direct activity, such as an association with or an enzymatic activity on a second protein, or an indirect activity, such as a cellular signaling activity mediated by interaction of the ATPase-like protein with a second protein. In a preferred embodiment, an ATPase-like activity includes at least one or more of the following activities: (1) modulating (stimulating and/or enhancing or inhibiting) cellular division; (2) modulating organelle biogenesis; (3) modulating protein sorting; (4) modulating gene expression; (5) modulating protein degradation; and (6) modulating the function of the 26S proteosome.

An "isolated" or "purified" ATPase-like nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated ATPase-like nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. An ATPase-like protein that is substantially free of cellular material includes preparations of ATPase-like protein having less than about 30%, 20%, 10%, or 5% (by dry weight) of non-ATPase protein (also referred to herein as a "contaminating protein"). When the ATPase-like protein or biologically active portion thereof is recombinantly produced, preferably, culture medium represents less than about 30%, 20%, 10%, or 5% of the volume of the protein preparation. When ATPase-like protein is produced by chemical synthesis, preferably the protein preparations have less than about 30%, 20%, 10%, or 5% (by dry weight) of chemical precursors or non-ATPase chemicals.

Various aspects of the invention are described in further detail in the following subsections.

I. Isolated Nucleic Acid Molecules

One aspect of the invention pertains to isolated nucleic acid molecules comprising nucleotide sequences encoding ATPase-like proteins and polypeptides or biologically active portions thereof, as well as nucleic acid molecules sufficient for use as hybridization probes to identify ATPase-like-encoding nucleic acids (e.g., ATPase-like mRNA) and fragments for use as PCR primers for the amplification or mutation of ATPase-like nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

Nucleotide sequences encoding the ATPase-like proteins of the present invention include sequences set forth in SEQ ID NO:1, 3, and complements thereof. By "complement" is intended a nucleotide sequence that is sufficiently complementary to a given nucleotide sequence such that it can hybridize to the given nucleotide sequence to thereby form a stable duplex. The corresponding amino acid sequence for the ATPase-like protein encoded by these nucleotide sequences is set forth in SEQ ID NO:2. The invention also encompasses nucleic acid molecules comprising nucleotide sequences encoding partial-length ATPase-like proteins, including the sequence set forth in SEQ ID NO:1, 3, and complements thereof Nucleic acid molecules that are fragments of these ATPase-like nucleotide sequences are also encompassed by the present invention. By "fragment" is intended a portion of the nucleotide sequence encoding an ATPase-like protein. A fragment of an ATPase-like nucleotide sequence may encode a biologically active portion of an ATPase-like protein, or it may be a fragment that can be used as a hybridization probe or PCR primer using methods disclosed below. A biologically active portion of an ATPase-like protein can be prepared by isolating a portion of one of the ATPase-like nucleotide sequences of the invention, expressing the encoded portion of the ATPase-like protein (e.g., by recombinant expression in vitro), and assessing the activity of the encoded portion of the ATPase-like protein. Nucleic acid molecules that are fragments of an ATPase-like nucleotide sequence comprise at least 15, 20, 50, 75, 100, 200, 300, 350, 400, 450, 500, 550, 600, 650, 700, 750, 800, 850, 900, 950, 1000, 1050, 1100, 1150, 1200, 1250, 1300, 1350, 1400 nucleotides, or up to the number of nucleotides present in a full-length ATPase-like nucleotide sequence disclosed herein (for example, 1748 nucleotides for SEQ ID NO:1 and 1086 nucleotides for SEQ ID NO:3) depending upon the intended use. Alternatively, a nucleic acid molecules that is a fragment of an ATPase-like nucleotide sequence of the present invention comprises a nucleotide sequence consisting of nucleotides 1–100, 100–200, 200–300, 300–400, 400–500, 500–600, 600–700, 700–800, 800–900, 900–1086, 1086–1100, 1100–1200, 1200–1300, 1300–1400, 1400–1500, 1500–1600, 1600–1700, or 1700–1748 of SEQ ID NO:1 or 3.

It is understood that isolated fragments include any contiguous sequence not disclosed prior to the invention as well as sequences that are substantially the same and which are not disclosed. Accordingly, if an isolated fragment is disclosed prior to the present invention, that fragment is not intended to be encompassed by the invention. When a sequence is not disclosed prior to the present invention, an isolated nucleic acid fragment is at least about 12, 15, 20, 25, or 30 contiguous nucleotides. Other regions of the nucleotide sequence may comprise fragments of various sizes, depending upon potential homology with previously disclosed sequences.

A fragment of an ATPase-like nucleotide sequence that encodes a biologically active portion of an ATPase-like protein of the invention will encode at least 15, 25, 30, 50, 75, 100, 125, 150, 175, 200, 250, or 300 contiguous amino acids, or up to the total number of amino acids present in a full-length ATPase-like protein of the invention (for example, 362 amino acids). Fragments of an ATPase-like nucleotide sequence that are useful as hybridization probes for PCR primers generally need not encode a biologically active portion of an ATPase-like protein.

Nucleic acid molecules that are variants of the ATPase-like nucleotide sequences disclosed herein are also encompassed by the present invention. "Variants" of the ATPase-like nucleotide sequences include those sequences that encode the ATPase-like proteins disclosed herein but that differ conservatively because of the degeneracy of the genetic code. These naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the ATPase-like proteins disclosed in the present invention as discussed below. Generally, nucleotide sequence variants of the invention will have at least 45%, 55%, 65%, 75%, 85%, 95%, or 98% identity to a particular nucleotide sequence disclosed herein. A variant ATPase-like nucleotide sequence will encode an ATPase-like protein that has an amino acid sequence having at least 45%, 55%, 65%, 75%, 85%, 95%, or 98% identity to the amino acid sequence of an ATPase-like protein disclosed herein.

In addition to the ATPase-like nucleotide sequences shown in SEQ ID NOS:1 and 3, it will be appreciated by those skilled in the art that DNA sequence polymorphisms that lead to changes in the amino acid sequences of ATPase-like proteins may exist within a population (e.g., the human population). Such genetic polymorphism in an ATPase-like gene may exist among individuals within a population due to natural allelic variation. An allele is one of a group of genes that occur alternatively at a given genetic locus. As used herein, the terms "gene" and "recombinant gene" refer to nucleic acid molecules comprising an open reading frame encoding an ATPase-like protein, preferably a mammalian ATPase-like protein. As used herein, the phrase "allelic variant" refers to a nucleotide sequence that occurs at an ATPase-like locus or to a polypeptide encoded by the nucleotide sequence. Such natural allelic variations can typically result in 1–5% variance in the nucleotide sequence of the ATPase-like gene. Any and all such nucleotide variations and resulting amino acid polymorphisms or variations in an ATPase-like sequence that are the result of natural allelic variation and that do not alter the functional activity of ATPase-like proteins are intended to be within the scope of the invention.

Moreover, nucleic acid molecules encoding ATPase-like proteins from other species (ATPase-like homologues), which have a nucleotide sequence differing from that of the ATPase-like sequences disclosed herein, are intended to be within the scope of the invention. For example, nucleic acid molecules corresponding to natural allelic variants and homologues of the human ATPase-like cDNA of the invention can be isolated based on their identity to the human ATPase-like nucleic acid disclosed herein using the human cDNA, or a portion thereof, as a hybridization probe according to standard hybridization techniques under stringent hybridization conditions as disclosed below.

In addition to naturally-occurring allelic variants of the ATPase-like sequences that may exist in the population, the skilled artisan will further appreciate that changes can be introduced by mutation into the nucleotide sequences of the invention thereby leading to changes in the amino acid sequence of the encoded ATPase-like proteins, without altering the biological activity of the ATPase-like proteins. Thus, an isolated nucleic acid molecule encoding an ATPase-like protein having a sequence that differs from that of SEQ ID NO:2 can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, preferably, conservative amino acid substitutions may be made at one or more predicted, preferably nonessential amino acid residues. A "nonessential" amino acid residue is a residue that can be altered from the wild-type sequence of an ATPase-like protein (e.g., the sequence of SEQ ID NO:2) without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Such substitutions would not be made for conserved amino acid residues, or for amino acid residues residing within a conserved motif, such as the growth factor and cytokine receptor signature 2 sequence and the U-PAR/Ly-6 domain sequence of SEQ ID NO:2, where such residues are essential for protein activity.

Alternatively, variant ATPase-like nucleotide sequences can be made by introducing mutations randomly along all or part of an ATPase-like coding sequence, such as by saturation mutagenesis, and the resultant mutants can be screened for ATPase-like biological activity to identify mutants that retain activity. Following mutagenesis, the encoded protein can be expressed recombinantly, and the activity of the protein can be determined using standard assay techniques.

Thus the nucleotide sequences of the invention include the sequences disclosed herein as well as fragments and variants thereof The ATPase-like nucleotide sequences of the invention, and fragments and variants thereof, can be used as probes and/or primers to identify and/or clone ATPase-like homologues in other cell types, e.g., from other tissues, as well as ATPase-like homologues from other mammals. Such probes can be used to detect transcripts or genomic sequences encoding the same or identical proteins. These probes can be used as part of a diagnostic test kit for identifying cells or tissues that misexpress an ATPase-like protein, such as by measuring levels of an ATPase-like-encoding nucleic acid in a sample of cells from a subject, e.g., detecting ATPase-like mRNA levels or determining whether a genomic ATPase-like gene has been mutated or deleted.

In this manner, methods such as PCR, hybridization, and the like can be used to identify such sequences having substantial identity to the sequences of the invention. See, for example, Sambrook et al. (1989) *Molecular Cloning: Laboratory Manual* (2d ed., Cold Spring Harbor Laboratory Press, Plainview, N.Y.) and Innis, et al. (1990) *PCR Protocols: A Guide to Methods and Applications* (Academic Press, N.Y.). ATPase-like nucleotide sequences isolated based on their sequence identity to the ATPase-like nucleotide sequences set forth herein or to fragments and variants thereof are encompassed by the present invention.

In a hybridization method, all or part of a known ATPase-like nucleotide sequence can be used to screen cDNA or genomic libraries. Methods for construction of such cDNA and genomic libraries are generally known in the art and are disclosed in Sambrook et al. (1989) *Molecular Cloning: A Laboratory Manual* (2d ed, Cold Spring Harbor Laboratory Press, Plainview, N.Y.). The so-called hybridization probes may be genomic DNA fragments, cDNA fragments, RNA fragments, or other oligonucleotides, and may be labeled with a detectable group such as $^{32}P$, or any other detectable marker, such as other radioisotopes, a fluorescent compound, an enzyme, or an enzyme co-factor. Probes for hybridization can be made by labeling synthetic oligonucleotides based on the known ATPase-like nucleotide sequence disclosed herein. Degenerate primers designed on the basis of conserved nucleotides or amino acid residues in a known ATPase-like nucleotide sequence or encoded amino acid sequence can additionally be used. The probe typically comprises a region of nucleotide sequence that hybridizes under stringent conditions to at least about 12, preferably about 25, more preferably about 50, 75, 100, 125, 150, 175, 200, 250, 300, 350, or 400 consecutive nucleotides of an ATPase-like nucleotide sequence of the invention or a fragment or variant thereof. Preparation of probes for hybridization is generally known in the art and is disclosed in Sambrook et al. (1989) *Molecular Cloning: A Laboratory Manual* (2d ed., Cold Spring Harbor Laboratory Press, Plainview, N.Y.), herein incorporated by reference.

For example, in one embodiment, a previously unidentified ATPase-like nucleic acid molecule hybridizes under stringent conditions to a probe that is a nucleic acid molecule comprising one of the ATPase-like nucleotide sequences of the invention or a fragment thereof. In another embodiment, the previously unknown ATPase-like nucleic acid molecule is at least 300, 325, 350, 375, 400, 425, 450, 500, 550, 600, 650, 700, 800, 900, 1000, 2,000, 3,000, 4,000 or 5,000 nucleotides in length and hybridizes under stringent conditions to a probe that is a nucleic acid molecule comprising one of the ATPase-like nucleotide sequences disclosed herein or a fragment thereof.

Accordingly, in another embodiment, an isolated previously unknown ATPase-like nucleic acid molecule of the invention is at least 300, 325, 350, 375, 400, 425, 450, 500, 550, 600, 650, 700, 800, 900, 1000, 1,100, 1,200, 1,300, or 1,400 nucleotides in length and hybridizes under stringent conditions to a probe that is a nucleic acid molecule comprising one of the nucleotide sequences of the invention, preferably the coding sequence set forth in SEQ ID NO:1, 3, or a complement, fragment, or variant thereof.

As used herein, the term "hybridizes under stringent conditions" is intended to describe conditions for hybridization and washing under which nucleotide sequences typically remain hybridized to each other. Such stringent conditions are known to those skilled in the art and can be found in *Current Protocols in Molecular Biology* (John Wiley & Sons, New York (1989)), 6.3.1–6.3.6. A preferred, example of stringent hybridization conditions are hybridization in 6× sodium chloride/sodiurn citrate (SSC) at about 45° C., followed by one or more washes in 0.2×SSC, 0.1% SDS at 50° C. Another example of stringent hybridization conditions are hybridization in 6× sodium chloride/sodium citrate (SSC) at about 45° C., followed by one or more washes in 0.2×SSC, 0.1% SDS at 55° C. A further example of stringent hybridization conditions are hybridization in 6× sodium chloride/sodium citrate (SSC) at about 45° C., followed by one or more washes in 0.2×SSC, 0.1% SDS at 60° C. Preferably, stringent hybridization conditions are hybridization in 6× sodium chloride/sodium citrate (SSC) at about 45° C., followed by one or more washes in 0.2×SSC, 0.1% SDS at 65° C. Particularly preferred stringency conditions (and the conditions that should be used if the practitioner is uncertain about what conditions should be applied to determine if a molecule is within a hybridization limitation of the invention) are 0.5M Sodium Phosphate, 7% SDS at 65° C., followed by one or more washes at 0.2×SSC, 1% SDS at 65° C. Preferably, an isolated nucleic acid molecule that hybridizes under stringent conditions to an ATPase-like sequence of the invention corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

Thus, in addition to the ATPase-like nucleotide sequences disclosed herein and fragments and variants thereof, the isolated nucleic acid molecules of the invention also encompass homologous DNA sequences identified and isolated from other cells and/or organisms by hybridization with entire or partial sequences obtained from the ATPase-like nucleotide sequences disclosed herein or variants and fragments thereof.

The present invention also encompasses antisense nucleic acid molecules, i.e., molecules that are complementary to a sense nucleic acid encoding a protein, e.g., complementary to the coding strand of a double-stranded cDNA molecule, or complementary to an mRNA sequence. Accordingly, an antisense nucleic acid can hydrogen bond to a sense nucleic acid. The antisense nucleic acid can be complementary to an entire ATPase-like coding strand, or to only a portion thereof, e.g., all or part of the protein coding region (or open reading frame). An antisense nucleic acid molecule can be antisense to a noncoding region of the coding strand of a nucleotide sequence encoding an ATPase-like protein. The noncoding regions are the 5' and 3' sequences that flank the coding region and are not translated into amino acids.

Given the coding-strand sequence encoding an ATPase-like protein disclosed herein (e.g., SEQ ID NO:1), antisense nucleic acids of the invention can be designed according to the rules of Watson and Crick base pairing. The antisense nucleic acid molecule can be complementary to the entire coding region of ATPase-like mRNA, but more preferably is an oligonucleotide that is antisense to only a portion of the coding or noncoding region of ATPase-like mRNA. For example, the antisense oligonucleotide can be complementary to the region surrounding the translation start site of ATPase-like mRNA. An antisense oligonucleotide can be, for example, about 5, 10, 15, 20, 25, 30, 35, 40, 45, or 50 nucleotides in length. An antisense nucleic acid of the invention can be constructed using chemical synthesis and enzymatic ligation procedures known in the art.

For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, including, but not limited to, for example e.g., phosphorothioate derivatives and acridine substituted nucleotides. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding an ATPase-like protein to thereby inhibit expression of the protein, e.g., by inhibiting transcription and/or translation. An example of a route of administration of antisense nucleic acid molecules of the invention includes direct injection at a tissue site. Alternatively, antisense nucleic acid molecules can be modified to target selected cells and then administered systemically. For example, antisense molecules can be linked to peptides or antibodies to form a complex that specifically binds to receptors or antigens expressed on a selected cell surface. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

The invention also encompasses ribozymes, which are catalytic RNA molecules with ribonuclease activity that are capable of cleaving a single-stranded nucleic acid, such as an mRNA, to which they have a complementary region. Ribozymes (e.g., hammerhead ribozymes (described in Haselhoff and Gerlach (1988) *Nature* 334:585–591)) can be used to catalytically cleave ATPase-like mRNA transcripts to thereby inhibit translation of ATPase-like mRNA. A ribozyme having specificity for an ATPase-like—encoding nucleic acid can be designed based upon the nucleotide sequence of an ATPase-like cDNA disclosed herein (e.g., SEQ ID NO:1). See, e.g., Cech et al., U.S. Pat. No. 4,987,071; and Cech et al., U.S. Pat. No. 5,116,742. Alternatively, ATPase-like mRNA can be used to select a catalytic RNA having a specific ribonuclease activity from a pool of RNA molecules. See, e.g., Bartel and Szostak (1993) *Science* 261:1411–1418.

The invention also encompasses nucleic acid molecules that form triple helical structures. For example, ATPase-like gene expression can be inhibited by targeting nucleotide sequences complementary to the regulatory region of the ATPase-like protein (e.g., the ATPase-like promoter and/or enhancers) to form triple helical structures that prevent transcription of the ATPase-like gene in target cells. See generally Helene (1991) *Anticancer Drug Des.* 6(6): 569; Helene (1992) *Ann. N.Y. Acad. Sci.* 660:27; and Maher (1992) *Bioassays* 14(12): 807.

In preferred embodiments, the nucleic acid molecules of the invention can be modified at the base moiety, sugar moiety, or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4:5). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid-phase peptide synthesis protocols as described in Hyrup et al. (1996), supra; Perry-O'Keefe et al. (1996) *Proc. Natl. Acad. Sci. USA* 93:14670.

PNAs of an ATPase-like molecule can be used in therapeutic and diagnostic applications. For example, PNAs can be used as antisense or antigene agents for sequence-specific modulation of gene expression by, e.g., inducing transcription or translation arrest or inhibiting replication. PNAs of the invention can also be used, e.g., in the analysis of single base pair mutations in a gene by, e.g., PNA-directed PCR clamping, as artificial restriction enzymes when used in combination with other enzymes, e.g., S1 nucleases (Hyrup (1996), supra; or as probes or primers for DNA sequence and hybridization (Hyrup (1996), supra; Periy-O'Keefe et al. (1996), supra).

In another embodiment, PNAs of an ATPase-like molecule can be modified, e.g., to enhance their stability, specificity, or cellular uptake, by attaching lipophilic or other helper groups to PNA, by the formation of PNA-DNA chimeras, or by the use of liposomes or other techniques of drug delivery known in the art. The synthesis of PNA-DNA chimeras can be performed as described in Hyrup (1996), supra; Finn et al. (1996) *Nucleic Acids Res.* 24(17): 3357–63; Mag et al. (1989) *Nucleic Acids Res.* 17:5973; and Peterson et al. (1975) *Bioorganic Med. Chem. Lett.* 5:1119.

II. Isolated ATPase-like Proteins and Anti-ATPase-like Antibodies

ATPase-like proteins are also encompassed within the present invention. By "ATPase-like protein" is intended a protein having the amino acid sequence set forth in SEQ ID NO:2, as well as fragments, biologically active portions, and variants thereof.

"Fragments" or "biologically active portions" include polypeptide fragments suitable for use as immunogens to raise anti-ATPase-like antibodies. Fragments include peptides comprising amino acid sequences sufficiently identical to or derived from the amino acid sequence of an ATPase-like protein, or partial-length protein, of the invention and exhibiting at least one activity of an ATPase-like protein, but which include fewer amino acids than the full-length (SEQ ID NO:2) ATPase-like protein disclosed herein. Typically, biologically active portions comprise a domain or motif with at least one activity of the ATPase-like protein. A biologically active portion of an ATPase-like protein can be a polypeptide which is, for example, 10, 25, 50, 100 or more amino acids in length. Such biologically active portions can be prepared by recombinant techniques and evaluated for one or more of the functional activities of a native ATPase-like protein. As used here, a fragment comprises at least 5 contiguous amino acids of SEQ ID NO:2. The invention encompasses other fragments, however, such as any fragment in the protein greater than 6, 7, 8, or 9 amino acids.

By "variants" is intended proteins or polypeptides having an amino acid sequence that is at least about 45%, 55%, 65%, preferably about 75%, 85%, 95%, or 98% identical to the amino acid sequence of SEQ ID NO:2. Variants also include polypeptides encoded by a nucleic acid molecule that hybridizes to the nucleic acid molecule of SEQ ID NO:2, or a complement thereof, under stringent conditions. In another embodiment, a variant of an isolated polypeptide of the present invention differs, by at least 1, but less than 5, 10, 20, 50, or 100 amino acid residues from the sequence shown in SEQ ID NO:2. If alignment is needed for this comparison the sequences should be aligned for maximum identity. "Looped" out sequences from deletions or insertions, or mismatches, are considered differences. Such variants generally retain the functional activity of the ATPase-like proteins of the invention. Variants include polypeptides that differ in amino acid sequence due to natural allelic variation or mutagenesis.

The invention also provides ATPase-like chimeric or fusion proteins. As used herein, an ATPase-like "chimeric protein" or "fusion protein" comprises an ATPase-like polypeptide operably linked to a non-ATPase polypeptide. An "ATPase-like polypeptide" refers to a polypeptide having an amino acid sequence corresponding to an ATPase-like protein, whereas a "non-ATPase-like polypeptide" refers to a polypeptide having an amino acid sequence corresponding to a protein that is not substantially identical to the ATPase-like protein, e.g., a protein that is different from the ATPase-like protein and which is derived from the same or a different organism. Within an ATPase-like fusion protein, the ATPase-like polypeptide can correspond to all or a portion of an ATPase-like protein, preferably at least one biologically active portion of an ATPase-like protein. Within the fusion protein, the term "operably linked" is intended to indicate that the ATPase-like polypeptide and the non-ATPase-like polypeptide are fused in-frarne to each other. The non-ATPase-like polypeptide can be fused to the N-terminus or C-terminus of the ATPase-like polypeptide.

One useful fusion protein is a GST-ATPase-like fusion protein in which the ATPase-like sequences are fused to the C-tenninus of the GST sequences. Such fusion proteins can facilitate the purification of recombinant ATPase-like proteins.

In yet another embodiment, the fusion protein is an ATPase-like-immunoglobulin fusion protein in which all or part of an ATPase-like protein is fused to sequences derived from a member of the immunoglobulin protein family. The ATPase-like-immunoglobulin fusion proteins of the invention can be incorporated into pharmaceutical compositions and administered to a subject to inhibit an interaction between an ATPase-like ligand and an ATPase-like protein on the surface of a cell, thereby suppressing ATPase-like-mediated signal transduction in vivo. The ATPase-like-immunoglobulin fusion proteins can be used to affect the bioavailability of an ATPase-like cognate ligand. Inhibition of the ATPase-like ligand/ATPase-like interaction may be useful therapeutically, both for treating proliferative and differentiative disorders and for modulating (e.g., promoting or inhibiting) cell survival. Moreover, the ATPase-like-immunoglobulin fusion proteins of the invention can be used as immunogens to produce anti-ATPase-like antibodies in a subject, to purify ATPase-like ligands, and in screening assays to identify molecules that inhibit the interaction of an ATPase-like protein with an ATPase-like ligand.

Preferably, an ATPase-like chimeric or fusion protein of the invention is produced by standard recombinant DNA techniques. For example, DNA fragments coding for the different polypeptide sequences may be ligated together in-frame, or the fusion gene can be synthesized, such as with automated DNA synthesizers. Alternatively, PCR amplification of gene fragments can be carried out using anchor primers that give rise to complementary overhangs between two consecutive gene fragments, which can subsequently be annealed and reamplified to generate a chimeric gene sequence (see, e.g., Ausubel et al., eds. (1995) *Current Protocols in Molecular Biology*) (Greene Publishing and Wiley-Interscience, NY). Moreover, an ATPase-like-encoding nucleic acid can be cloned into a commercially available expression vector such that it is linked in-frame to an existing fusion moiety. Variants of the ATPase-like proteins can function as either ATPase-like agonists (mimetics) or as ATPase-like antagonists. Variants of the ATPase-like protein can be generated by mutagenesis, e.g., discrete point mutation or truncation of the ATPase-like protein. An agonist of the ATPase-like protein can retain substantially the same, or a subset, of the biological activities of the naturally occurring form of the ATPase-like protein. An antagonist of the ATPase-like protein can inhibit one or more of the activities of the naturally occurring form of the ATPase-like protein by, for example, competitively binding to a downstream or upstream member of a cellular signaling cascade that includes the ATPase-like protein. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the ATPase-like proteins.

Variants of an ATPase-like protein that function as either ATPase-like agonists or as ATPase-like antagonists can be identified by screening combinatorial libraries of mutants, e.g., truncation mutants, of an ATPase-like protein for ATPase-like protein agonist or antagonist activity. In one embodiment, a variegated library of ATPase-like variants is generated by combinatorial mutagenesis at the nucleic acid level and is encoded by a variegated gene library. A variegated library of ATPase-like variants can be produced by, for example, enzymatically ligating a mixture of synthetic oligonucleotides into gene sequences such that a degenerate set of potential ATPase-like sequences is expressible as individual polypeptides, or alternatively, as a set of larger fusion proteins (e.g., for phage display) containing the set of ATPase-like sequences therein. There are a variety of methods that can be used to produce libraries of potential ATPase-like variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential ATPase-like sequences. Methods for synthesizing degenerate oligonucleotides are known in the art (see, e.g., Narang (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477).

In addition, libraries of fragments of an ATPase-like protein coding sequence can be used to generate a variegated population of ATPase-like fragments for screening and subsequent selection of variants of an ATPase-like protein. In one embodiment, a library of coding sequence fragments can be generated by treating a double-stranded PCR fragment of an ATPase-like coding sequence with a nuclease under conditions wherein nicking occurs only about once per molecule, denaturing the double-stranded DNA, renaturing the DNA to form double-stranded DNA which can include sense/antisense pairs from different nicked products, removing single-stranded portions from reformed duplexes by treatment with S1 nuclease, and ligating the resulting fragment library into an expression vector. By this method, one can derive an expression library that encodes N-terminal and internal fragments of various sizes of the ATPase-like protein.

Several techniques are known in the art for screening gene products of combinatorial libraries made by point mutations or truncation and for screening cDNA libraries for gene products having a selected property. Such techniques are adaptable for rapid screening of the gene libraries generated by the combinatorial mutagenesis of ATPase-like proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique that enhances the frequency of functional mutants in the libraries, can be used in combination with the screening assays to identify ATPase-like variants (Arkin and Yourvan (1992) *Proc. Natl. Acad. Sci. USA* 89:7811–7815; Delgrave et al. (1993) *Protein Engineering* 6(3): 327–331).

An isolated ATPase-like polypeptide of the invention can be used as an immunogen to generate antibodies that bind ATPase-like proteins using standard techniques for polyclonal and monoclonal antibody preparation. The full-length ATPase-like protein can be used or, alternatively, the invention provides antigenic peptide fragments of ATPase-like proteins for use as immunogens. The antigenic peptide of an ATPase-like protein comprises at least 8, preferably 10, 15, 20, or 30 amino acid residues of the amino acid sequence shown in SEQ ID NO:2 and encompasses an epitope of an ATPase-like protein such that an antibody raised against the peptide forms a specific immune complex with the ATPase-like protein. Preferred epitopes encompassed by the antigenic peptide are regions of a ATPase-like protein that are located on the surface of the protein, e.g., hydrophilic regions.

Accordingly, another aspect of the invention pertains to anti-ATPase-like polyclonal and monoclonal antibodies that bind an ATPase-like protein. Polyclonal anti-ATPase-like antibodies can be prepared by immunizing a suitable subject (e.g., rabbit, goat, mouse, or other mammal) with an ATPase-like immunogen. The anti-ATPase-like antibody titer in the immunized subject can be monitored over time by standard techniques, such as with an enzyme linked immunosorbent assay (ELISA) using immobilized ATPase-like protein. At an appropriate time after immunization, e.g., when the anti-ATPase-like antibody titers are highest, antibody-producing cells can be obtained from the subject and used to prepare monoclonal antibodies by standard techniques, such as the hybridoma technique originally described by Kohler and Milstein (1975) *Nature* 256:495–497, the human B cell hybridoma technique (Kozbor et al. (1983) *Immunol. Today* 4:72), the EBV-hybridoma technique (Cole et al. (1985) in *Monoclonal Antibodies and Cancer Therapy*, ed. Reisfeld and Sell (Alan R. Liss, Inc., New York, N.Y.), pp. 77–96) or trioma techniques. The technology for producing hybridomas is well known (see generally Coligan et al., eds. (1994) *Current Protocols in Immunology* (John Wiley & Sons, Inc., New York, N.Y.); Galfre et al. (1977) *Nature* 266:55052; Kenneth (1980) in *Monoclonal Antibodies: A New Dimension In Biological Analyses* (Plenum Publishing Corp., NY; and Lerner (1981) *Yale J. Biol. Med.*, 54:387–402).

Alternative to preparing monoclonal antibody-secreting hybridomas, a monoclonal anti-ATPase-like antibody can be identified and isolated by screening a recombinant combinatorial immunoglobulin library (e.g., an antibody phage display library) with an ATPase-like protein to thereby isolate immunoglobulin library members that bind the ATPase-like protein. Kits for generating and screening phage display libraries are commercially available (e.g., the Pharmacia *Recombinant Phage Antibody System*, Catalog No. 27-9400-01, and the Stratagene SurfZAP™ *Phage Display Kit*, Catalog No. 240612). Additionally, examples of methods and reagents particularly amenable for use in generating and screening antibody display library can be found in, for example, U.S. Pat. No. 5,223,409; PCT Publication Nos. WO 92/18619; WO 91/17271; WO 92/20791; WO 92/15679; 93/01288; WO 92/01047; 92/09690; and 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J.* 12:725–734.

Additionally, recombinant anti-ATPase-like antibodies, such as chimeric and humanized monoclonal antibodies, comprising both human and nonhuman portions, which can be made using standard recombinant DNA techniques, are within the scope of the invention. Such chimeric and humanized monoclonal antibodies can be produced by recombinant DNA techniques known in the art, for example using methods described in PCT Publication Nos. WO 86101533 and WO 87/02671; European Patent Application Nos. 184,187, 171,496, 125,023, and 173,494; U.S. Pat. Nos. 4,816,567 and 5,225,539; European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; Shaw et al. (1988) *J. Natl. Cancer Inst.* 80:1553–1559); Morrison (1985) *Science* 229:1202–1207; Oi et al. (1986) *Bio/Techniques* 4:214; Jones et al. (1986) *Nature* 321:552–525; Verhoeyan et al. (1988) *Science* 239:1534; and Beidler et al. (1988) *J. Immunol.* 141:4053–4060.

Completely human antibodies are particularly desirable for therapeutic treatment of human patients. Such antibodies can be produced using transgenic mice that are incapable of expressing endogenous immunoglobulin heavy and light chains genes, but which can express human heavy and light chain genes. See, for example, Lonberg and Huszar (1995) *Int. Rev. Immunol.* 13:65–93); and U.S. Pat. Nos. 5,625,126; 5,633,425; 5,569,825; 5,661,016; and 5,545,806. In addition, companies such as Abgenix, Inc. (Freemont, Calif.), can be engaged to provide human antibodies directed against a selected antigen using technology similar to that described above.

Completely human antibodies that recognize a selected epitope can be generated using a technique referred to as "guided selection." In this approach a selected non-human monoclonal antibody, e.g., a murine antibody, is used to guide the selection of a completely human antibody recognizing the same epitope. This technology is described by Jespers et al. (1994) *Bio/Technology* 12:899–903).

An anti-ATPase-like antibody (e.g., monoclonal antibody) can be used to isolate ATPase-like proteins by standard techniques, such as affinity chromatography or immunoprecipitation. An anti-ATPase-like antibody can facilitate the purification of natural ATPase-like protein from cells and of recombinantly produced ATPase-like protein expressed in host cells. Moreover, an anti-ATPase-like antibody can be used to detect ATPase-like protein (e.g., in a cellular lysate or cell supernatant) in order to evaluate the abundance and pattern of expression of the ATPase-like protein. Anti-ATPase-like antibodies can be used diagnostically to monitor protein levels in tissue as part of a clinical testing procedure, e.g., to, for example, determine the efficacy of a given treatment regimen. Detection can be facilitated by coupling the antibody to a detectable substance.

Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{35}$S, or $^{3}$H.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84:Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev., 62:119–58 (1982). Alternatively, an antibody can be conjugated to a second antibody to form an antibody heteroconjugate as described by Segal in U.S. Pat. No. 4,676,980.

III. Recombinant Expression Vectors and Host Cells

Another aspect of the invention pertains to vectors, preferably expression vectors, containing a nucleic acid encoding an ATPase-like protein (or a portion thereof). "Vector" refers to a nucleic acid molecule capable of transporting another nucleic acid to which it has been linked, such as a "plasmid", a circular double-stranded DNA loop into which additional DNA segments can be ligated, or a viral vector, where additional DNA segments can be ligated into the viral genome. The vectors are useful for autonomous replication in a host cell or may be integrated into the genome of a host cell upon introduction into the host cell, and thereby are replicated along with the host genome (e.g., nonepisomal mammalian vectors). Expression vectors are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses, and adeno-associated viruses), that serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, operably linked to the nucleic acid sequence to be expressed. "Operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers, and other expression control elements (e.g., polyadenylation signals). See, for example, Goeddel (1990) in *Gene Expression Technology: Methods in Enzymology* 185 (Academic Press, San Diego, Calif.). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., ATPase-like proteins, mutant forms of ATPase-like proteins, fusion proteins, etc.). It is further recognized that the nucleic acid sequences of the invention can be altered to contain codons, which are preferred, or non preferred, for a particular expression system. For example, the nucleic acid can be one in which at least one altered codon, and preferably at least 10%, or 20% of the codons have been altered such that the sequence is optimized for expression in *E. coli*, yeast, human, insect, or CHO cells. Methods for determining such codon usage are well known in the art.

The recombinant expression vectors of the invention can be designed for expression of ATPase-like protein in prokaryotic or eukaryotic host cells. Expression of proteins in prokaryotes is most often carried out in *E. coli* with vectors containing constitutive or inducible promoters directing the expression of either fusion or nonfusion proteins. Fusion vectors add a number of amino acids to a protein encoded therein, usually to the amino terminus of the recombinant protein. Typical fusion expression vectors include pGEX (Pharnacia Biotech Inc; Smith and Johnson (1988) *Gene* 67:31–40), pMAL (New England Biolabs, Beverly, Mass.), and pRIT5 (Pharmacia, Piscataway, N.J.) which fuse glutathione S-transferase (GST), maltose E binding protein, or protein A, respectively, to the target recombinant protein. Examples of suitable inducible nonfusion *E. coli* expression vectors include pTrc (Amann et al. (1988) *Gene* 69:301–315) and pET 11d (Studier et al. (1990) in *Gene Expression Technology: Methods in Enzymology* 185 (Academic Press, San Diego, Calif.), pp. 60–89). Strategies to maximize recombinant protein expression in *E. coli* can be found in Gottesman (1990) in *Gene Expression Technology: Methods in Enzymology* 185 (Academic Press, CA), pp. 119–128 and Wada et al. (1992) *Nucleic Acids Res.* 20:2111–2118. Target gene expression from the pTrc vector relies on host RNA polymerase transcription from a hybrid trp-lac fusion promoter.

Suitable eukaryotic host cells include insect cells (examples of Baculovirus vectors available for expression of proteins in cultured insect cells (e.g., Sf9 cells) include the pAc series (Smith et al. (1983) *Mol. Cell Biol.* 3:2156–2165) and the pVL series (Lucklow and Summers (1989) *Virology* 170:31–39)); yeast cells (examples of vectors for expression in yeast *S. cereivisiae* include pYepSec1 (Baldari et al. (1987) *EMBO J.* 6:229–234), pMFa (Kuijan and Herskowitz (1982) *Cell* 30:933–943), pJRY88 (Schultz et al. (1987) *Gene* 54:113–123), pYES2 (Invitrogen Corporation, San Diego, Calif.), and pPicZ (Invitrogen Corporation, San Diego, Calif.)); or mammalian cells (mammalian expression vectors include pCDM8 (Seed (1987) *Nature* 329:840) and pMT2PC (Kaufman et al. (1987) *EMBO J.* 6:187:195)). Suitable mammalian cells include Chinese hamster ovary cells (CHO) or COS cells. In mammalian cells, the expression vector's control functions are often provided by viral regulatory elements. For example, commonly used promoters are derived from polyoma, Adenovirus 2, cytomegalovirus, and Simian Virus 40. For other suitable expression systems for both prokaryotic and eukaryotic cells, see chapters 16 and 17 of Sambrook et al. (1989) *Molecular cloning: A Laboratory Manual* (2d ed., Cold Spring Harbor Laboratory Press, Plainview, N.Y.). See, Goeddel (1990) in *Gene Expression Technology: Methods in Enzymology* 185 (Academic Press, San Diego, Calif.). Alternatively, the recombinant expression vector can be transcribed and translated in vitro, for example using T7 promoter regulatory sequences and T7 polymerase.

The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell but are still included within the scope of the term as used herein. A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

In one embodiment, the expression vector is a recombinant mammalian expression vector that comprises tissue-specific regulatory elements that direct expression of the nucleic acid preferentially in a particular cell type. Suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873, 316 and European Application Patent Publication No. 264, 166). Developmentally-regulated promoters are also encompassed, for example the murine hox promoters (Kessel and Gruss (1990) *Science* 249:374–379), the α-fetoprotein promoter (Campes and Tilghman (1989) *Genes Dev.* 3:537–546), and the like.

The invention further provides a recombinant expression vector comprising a DNA molecule of the invention cloned into the expression vector in an antisense orientation. That is, the DNA molecule is operably linked to a regulatory sequence in a manner that allows for expression (by transcription of the DNA molecule) of an RNA molecule that is antisense to ATPase-like mRNA. Regulatory sequences operably linked to a nucleic acid cloned in the antisense orientation can be chosen to direct the continuous expression of the antisense RNA molecule in a variety of cell types, for instance viral promoters and/or enhancers, or regulatory sequences can be chosen to direct constitutive, tissue-specific, or cell-type-specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (1986) *Reviews—Trends in Genetics*, Vol. 1(1).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (1989) *Molecular Cloning: A Laboratory Manual* (2d ed., Cold Spring Harbor Laboratory Press, Plainview, N.Y.) and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin, and methotrexate. Nucleic acid encoding a selectable marker can be introduced into a host cell on the same vector as that encoding an ATPase-like protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) ATPase-like protein. Accordingly, the invention further provides methods for producing ATPase-like protein using the host cells of the invention. In one embodiment, the method comprises culturing the host cell of the invention, into which a recombinant expression vector encoding an ATPase-like protein has been introduced, in a suitable medium such that ATPase-like protein is produced. In another embodiment, the method further comprises isolating ATPase-like protein from the medium or the host cell.

The host cells of the invention can also be used to produce nonhuman transgenic animals. For example, in one embodiment, a host cell of the invention is a fertilized oocyte or an embryonic stem cell into which ATPase-like-coding sequences have been introduced. Such host cells can then be used to create nonhuman transgenic animals in which exogenous ATPase-like sequences have been introduced into their genome or homologous recombinant animals in which endogenous ATPase-like sequences have been altered. Such animals are useful for studying the function and/or activity of ATPase-like genes and proteins and for identifying and/or evaluating modulators of ATPase-like activity. As used herein, a "transgenic animal" is a nonhuman animal, preferably a mammal, more preferably a rodent such as a rat or mouse, in which one or more of the cells of the animal includes a transgene. Other examples of transgenic animals include nonhuman primates, sheep, dogs, cows, goats, chickens, amphibians, etc. A transgene is exogenous DNA that is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a nonhuman animal, preferably a mammal, more preferably a mouse, in which an endogenous ATPase-like gene has been altered by homologous recombination between the endogenous gene and an exogenous DNA molecule introduced into a cell of the animal, e.g., an embryonic cell of the animal, prior to development of the animal.

A transgenic animal of the invention can be created by introducing ATPase-like-encoding nucleic acid into the male pronuclei of a fertilized oocyte, e.g., by microinjection, retroviral infection, and allowing the oocyte to develop in a pseudopregnant female foster animal. The ATPase-like cDNA sequence can be introduced as a transgene into the genome of a nonhuman animal. Alternatively, a homologue of the mouse ATPase-like gene can be isolated based on hybridization and used as a transgene. Intronic sequences and polyadenylation signals can also be included in the transgene to increase the efficiency of expression of the transgene. A tissue-specific regulatory sequence(s) can be operably linked to the ATPase-like transgene to direct expression of ATPase-like protein to particular cells. Methods for generating transgenic animals via embryo manipulation and microinjection, particularly animals such as mice, have become conventional in the art and are described, for example, in U.S. Pat. Nos. 4,736,866, 4,870,009, and 4,873, 191 and in Hogan (1986) *Manipulating the Mouse Embryo* (Cold Spring Harbor Laboratory Press, Cold Spring Harbor, N.Y., 1986). Similar methods are used for production of other transgenic animals. A transgenic founder animal can be identified based upon the presence of the ATPase-like transgene in its genome and/or expression of ATPase-like mRNA in tissues or cells of the animals. A transgenic founder animal can then be used to breed additional animals carrying the transgene. Moreover, transgenic animals carrying a transgene encoding ATPase-like gene can further be bred to other transgenic animals carrying other transgenes.

To create a homologous recombinant animal, one prepares a vector containing at least a portion of an ATPase-like gene or a homolog of the gene into which a deletion, addition, or substitution has been introduced to thereby alter, e.g., functionally disrupt, the ATPase-like gene. In a preferred embodiment, the vector is designed such that, upon homologous recombination, the endogenous ATPase-like gene is functionally disrupted (i.e., no longer encodes a functional protein; also referred to as a "knock out" vector). Alternatively, the vector can be designed such that, upon homologous recombination, the endogenous ATPase-like gene is mutated or otherwise altered but still encodes functional protein (e.g., the upstream regulatory region can be altered to thereby alter the expression of the endogenous ATPase-like protein). In the homologous recombination vector, the altered portion of the ATPase-like gene is flanked at its 5' and 3' ends by additional nucleic acid of the ATPase-like gene to allow for homologous recombination to occur between the exogenous ATPase-like gene carried by the vector and an endogenous ATPase-like gene in an embryonic stem cell. The additional flanking ATPase-like nucleic acid is of sufficient length for successful homologous recombination with the endogenous gene. Typically, several kilobases of flanking DNA (both at the 5' and 3' ends) are included in the vector (see, e.g., Thomas and Capecchi (1987) *Cell* 51:503 for a description of homologous recombination vectors). The vector is introduced into an embryonic stem cell line (e.g., by electroporation), and cells in which the introduced ATPase-like gene has homologously recombined with the endogenous ATPase-like gene are selected (see, e.g., Li et al. (1992) *Cell* 69:915). The selected cells are then injected into a blastocyst of an animal (e.g., a mouse) to form aggregation chimeras (see, e.g., Bradley (1987) in *Teratocarcinomas and Embryonic Stem Cells: A Practical Approach*, ed. Robertson (IRL, Oxford pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Current Opinion in Bio/Technology* 2:823–829 and in PCT Publication Nos. WO 90/11354, WO 91/01140, WO 92/0968, and WO 93/04169.

In another embodiment, transgenic nonhuman animals containing selected systems that allow for regulated expression of the transgene can be produced. One example of such a system is the cre/loxP recombinase system of bacteriophage P1. For a description of the cred/loxP recombinase system, see, e.g., Lakso et al. (1992) *Proc. Natl. Acad. Sci. USA* 89:6232–6236. Another example of a recombinase system is the FLP recombinase system of *Saccharomyces cerevisiae* (O'Gorman et al. (1991) *Science* 251:1351–1355). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the nonhuman transgenic animals described herein can also be produced according to the methods described in Wilmut et al. (1997) *Nature* 385:810–813 and PCT Publication Nos. WO 97/07668 and WO 97/07669.

IV. Pharmaceutical Compositions

The ATPase-like nucleic acid molecules, ATPase-like proteins, and anti-ATPase-like antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The compositions of the invention are useful to treat any of the disorders discussed herein. The compositions are provided in therapeutically effective amounts. By "therapeutically effective amounts" is intended an amount sufficient to modulate the desired response. As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e,. including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the knowledge of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF; Parsippany, N.J.), or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof The proper fluidity can be maintained, for example, by the use of a coating such as lecithin, by the maintenance of the required particle size in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride, in the composition. Prolonged absorption of the injectable compositions can be brought about by including in the composition an agent that delays absorption, for example, aluminum monostearate and gelatin.

Sterile injectable solutions can be prepared by incorporating the active compound (e.g., an ATPase-like protein or anti-ATPase-like antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth, or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from a pressurized container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated with each unit containing a predetermined quantity of active compound calculated to produce the desired therapeutic effect in association with the required pharmaceutical carrier. Depending on the type and severity of the disease, about 1 $\mu$g/kg to about 15 mg/kg (e.g., 0.1 to 20 mg/kg) of antibody is an initial candidate dosage for administration to the patient, whether, for example, by one or more separate administrations, or by continuous infusion. A typical daily dosage might range from about 1 $\mu$g/kg to about 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays. An exemplary dosing regimen is disclosed in WO 94/04188. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (U.S. Pat. No. 5,328,470), or by stereotactic injection (see, e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: (a) screening assays; (b) detection assays (e.g., chromosomal mapping, tissue typing, forensic biology); (c) predictive medicine (e.g., diagnostic assays, prognostic assays, monitoring clinical trials, and pharmacogenomics); and (d) methods of treatment (e.g., therapeutic and prophylactic). The isolated nucleic acid molecules of the invention can be used to express ATPase-like protein (e.g., via a recombinant expression vector in a host cell in gene therapy applications), to detect ATPase-like mRNA (e.g., in a biological sample) or a genetic lesion in an ATPase-like gene, and to modulate ATPase-like activity. In addition, the ATPase-like proteins can be used to screen drugs or compounds that modulate the cellular activities described above as well as to treat disorders characterized by insufficient or excessive production of ATPase-like protein or production of ATPase-like protein forms that have decreased or aberrant activity compared to ATPase-like wild type protein. In addition, the anti-ATPase-like antibodies of the invention can be used to detect and isolate ATPase-like proteins and modulate ATPase-like activity.

A. Screening Assays

The invention provides a method (also referred to herein as a "screening assay") for identifying modulators, i.e., candidate or test compounds or agents (e.g., peptides, peptidomimetics, small molecules, or other drugs) that bind to ATPase-like proteins or have a stimulatory or inhibitory effect on, for example, ATPase-like expression or ATPase-like activity.

The test compounds of the present invention can be obtained using any of the numerous approaches in combinatorial library methods known in the art, including biological libraries, spatially addressable parallel solid phase or solution phase libraries, synthetic library methods requiring deconvolution, the "one-bead one-compound" library method, and synthetic library methods using affinity chromatography selection. The biological library approach is limited to peptide libraries, while the other four approaches are applicable to peptide, nonpeptide oligomer, or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422, Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *BioTechniques* 13:412–421), or on beads (Lam (1991) *Nature* 354:82–84), chips (Fodor (1993) *Nature* 364:555–556), bacteria (U.S. Pat. No. 5,223,409), spores (U.S. Pat. Nos. 5,571,698; 5,403,484; and 5,223,409), plasmids (Cull et al. (1992) *Proc. Natl. Acad. Sci. USA* 89:1865–1869), or phage (Scott and Smith (1990) *Science* 249:386–390; Devlin (1990) *Science* 249:404–406; Cwirla et al. (1990) *Proc. Natl. Acad. Sci. USA* 87:6378–6382; and Felici (1991) *J. Mol. Biol.* 222:301–310).

Determining the ability of the test compound to bind to the ATPase-like protein can be accomplished, for example, by coupling the test compound with a radioisotope or enzymatic label such that binding of the test compound to the ATPase-like protein or biologically active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemission or by scintillation counting. Alternatively, test compounds can be enzymatically labeled with, for example, horseradish peroxidase, alkaline phosphatase, or luciferase, and the enzymatic label detected by determination of conversion of an appropriate substrate to product.

In a similar manner, one may determine the ability of the ATPase-like protein to bind to or interact with an ATPase-like target molecule. By "target molecule" is intended a molecule with which an ATPase-like protein binds or interacts in nature. In a preferred embodiment, the ability of the ATPase-like protein to bind to or interact with an ATPase-like target molecule can be determined by monitoring the activity of the target molecule. For example, the activity of the target molecule can be monitored by detecting alterations in protein sorting, cell division, protein degradation, organelle biogenesis, etc., detecting catalytic/enzymatic activity of the target on an appropriate substrate, detecting the induction of a reporter gene (e.g., an ATPase-like-responsive regulatory element operably linked to a nucleic acid encoding a detectable marker, e.g. luciferase), or detecting a cellular response, for example, cellular differentiation or cell proliferation.

In yet another embodiment, an assay of the present invention is a cell-free assay comprising contacting an ATPase-like protein or biologically active portion thereof with a test compound and determining the ability of the test compound to bind to the ATPase-like protein or biologically active portion thereof. Binding of the test compound to the ATPase-like protein can be determined either directly or indirectly as described above. In a preferred embodiment, the assay includes contacting the ATPase-like protein or biologically active portion thereof with a known compound that binds ATPase-like protein to form an assay mixture, contacting the assay mixture with a test compound, and determining the ability of the test compound to preferentially bind to ATPase-like protein or biologically active portion thereof as compared to the known compound.

In another embodiment, an assay is a cell-free assay comprising contacting ATPase-like protein or biologically active portion thereof with a test compound and determining the ability of the test compound to modulate (e.g., stimulate or inhibit) the activity of the ATPase-like protein or biologically active portion thereof. Determining the ability of the test compound to modulate the activity of an ATPase-like protein can be accomplished, for example, by determining the ability of the ATPase-like protein to bind to an ATPase-like target molecule as described above for determining direct binding. In an alternative embodiment, determining the ability of the test compound to modulate the activity of an ATPase-like protein can be accomplished by determining the ability of the ATPase-like protein to further modulate an ATPase-like target molecule. For example, the catalytic/enzymatic activity of the target molecule on an appropriate substrate can be determined as previously described.

In yet another embodiment, the cell-free assay comprises contacting the ATPase-like protein or biologically active portion thereof with a known compound that binds an ATPase-like protein to form an assay mixture, contacting the assay mixture with a test compound, and determining the ability of the test compound to preferentially bind to or modulate the activity of an ATPase-like target molecule.

In the above-mentioned assays, it may be desirable to immobilize either an ATPase-like protein or its target molecule to facilitate separation of complexed from uncomplexed forms of one or both of the proteins, as well as to accommodate automation of the assay. In one embodiment, a fusion protein can be provided that adds a domain that allows one or both of the proteins to be bound to a matrix. For example, glutathione-S-transferase/ATPase-like fusion proteins or glutathione-S-transferase/target fusion proteins can be adsorbed onto glutathione sepharose beads (Sigma Chemical, St. Louis, Mo.) or glutathione-derivatized microtitre plates, which are then combined with the test compound or the test compound and either the nonadsorbed target protein or ATPase-like protein, and the mixture incubated under conditions conducive to complex formation (e.g., at physiological conditions for salt and pH). Following incubation, the beads or microtitre plate wells are washed to remove any unbound components and complex formation is measured either directly or indirectly, for example, as described above. Alternatively, the complexes can be dissociated from the matrix, and the level of ATPase-like binding or activity determined using standard techniques.

Other techniques for immobilizing proteins on matrices can also be used in the screening assays of the invention. For example, either ATPase-like protein or its target molecule can be immobilized utilizing conjugation of biotin and streptavidin. Biotinylated ATPase-like molecules or target molecules can be prepared from biotin-NHS (N-hydroxysuccinimide) using techniques well known in the art (e.g., biotinylation kit, Pierce Chemicals, Rockford, Ill.), and immobilized in the wells of streptavidin-coated 96-well plates (Pierce Chemicals). Alternatively, antibodies reactive with an ATPase-like protein or target molecules but which do not interfere with binding of the ATPase-like protein to its target molecule can be derivatized to the wells of the plate, and unbound target or ATPase-like protein trapped in the wells by antibody conjugation. Methods for detecting such complexes, in addition to those described above for the GST-immobilized complexes, include immunodetection of complexes using antibodies reactive with the ATPase-like protein or target molecule, as well as enzyme-linked assays that rely on detecting an enzymatic activity associated with the ATPase-like protein or target molecule.

In another embodiment, modulators of ATPase-like expression are identified in a method in which a cell is contacted with a candidate compound and the expression of ATPase-like mRNA or protein in the cell is determined relative to expression of ATPase-like mRNA or protein in a cell in the absence of the candidate compound When expression is greater (statistically significantly greater) in the presence of the candidate compound than in its absence, the candidate compound is identified as a stimulator of ATPase-like mRNA or protein expression. Alternatively, when expression is less (statistically significantly less) in the presence of the candidate compound than in its absence, the candidate compound is identified as an inhibitor of ATPase-like mRNA or protein expression. The level of ATPase-like mRNA or protein expression in the cells can be determined by methods described herein for detecting ATPase-like mRNA or protein.

In yet another aspect of the invention, the ATPase-like proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Bio/Techniques* 14:920–924; Iwabuchi et al. (1993) *Oncogene* 8:1693–1696; and PCT Publication No. WO 94/10300), to identify other proteins, which bind to or interact with ATPase-like protein ("ATPase-like-binding proteins" or "ATPase-like-bp") and modulate ATPase-like activity. Such ATPase-like-binding proteins are also likely to be involved in the propagation of signals by the ATPase-like proteins as, for example, upstream or downstream elements of the ATPase-like pathway.

This invention further pertains to novel agents identified by the above-described screening assays and uses thereof for treatments as described herein.

B. Detection Assays

Portions or fragments of the cDNA sequences identified herein (and the corresponding complete gene sequences) can be used in numerous ways as polynucleotide reagents. For example, these sequences can be used to: (1) map their respective genes on a chromosome; (2) identify an individual from a minute biological sample (tissue typing); and (3) aid in forensic identification of a biological sample. These applications are described in the subsections below.

1. Chromosome Mapping

The isolated complete or partial ATPase-like gene sequences of the invention can be used to map their respective ATPase-like genes on a chromosome, thereby facilitating the location of gene regions associated with genetic disease. Computer analysis of ATPase-like sequences can be used to rapidly select PCR primers (preferably 15–25 bp in length) that do not span more than one exon in the genomic DNA, thereby simplifying the amplification process. These primers can then be used for PCR screening of somatic cell hybrids containing individual human chromosomes. Only those hybrids containing the human gene corresponding to the ATPase-like sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow (because they lack a particular enzyme), but in which human cells can, the one human chromosome that contains the gene encoding the needed enzyme will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes (D'Eustachio et al. (1983) *Science* 220:919–924). Somatic cell hybrids containing only fragments of human chromosomes can also be produced by using human chromosomes with translocations and deletions.

Other mapping strategies that can similarly be used to map an ATPase-like sequence to its chromosome include in situ hybridization (described in Fan et al. (1990) *Proc. Natl. Acad. Sci. USA* 87:6223–27), pre-screening with labeled flow-sorted chromosomes, and pre-selection by hybridization to chromosome specific cDNA libraries. Furthermore, fluorescence in situ hybridization (FISH) of a DNA sequence to a metaphase chromosomal spread can be used to provide a precise chromosomal location in one step. For a review of this technique, see Verma eta. (1988) *Human Chromosomes: A Manual of Basic Techniques* (Pergamon Press, NY). The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results in a reasonable amount of time.

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Another strategy to map the chromosomal location of ATPase-like genes uses ATPase-like polypeptides and fragments and sequences of the present invention and antibodies specific thereto. This mapping can be carried out by specifically detecting the presence of a ATPase-like polypeptide in members of a panel of somatic cell hybrids between cells of a first species of animal from which the protein originates and cells from a second species of animal, and then determining which somatic cell hybrid(s) expresses the polypeptide and noting the chromosomes(s) from the first species of animal that it contains. For examples of this technique, see Pajunen et al. (1988) *Cytogenet. Cell. Genet.* 47:37–41 and Van Keuren et al. (1986) *Hum. Genet.* 74:34–40. Alternatively, the presence of a ATPase-like polypeptide in the somatic cell hybrids can be determined by assaying an activity or property of the polypeptide, for example, enzymatic activity, as described in Bordelon-Riser et al. (1979) *Somatic Cell Genetics* 5:597–613 and Owerbach et al. (1978) *Proc. Natl. Acad. Sci. USA* 75:5640–5644.

Once a sequence has been mapped to a precise chromosomal location, the physical position of the sequence on the chromosome can be correlated with genetic map data. (Such data are found, for example, in V. McKusick, *Mendelian Inheritance in Man*, available on-line through Johns Hopkins University Welch Medical Library). The relationship between genes and disease, mapped to the same chromosomal region, can then be identified through linkage analysis (co-inheritance of physically adjacent genes), described in, e.g., Egeland et al. (1987) *Nature* 325:783–787.

Moreover, differences in the DNA sequences between individuals affected and unaffected with a disease associated with the ATPase-like gene can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The ATPase-like sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes and probed on a Southern blot to yield unique bands for identification. The sequences of the present invention are useful as additional DNA markers for RFLP (described in U.S. Pat. No. 5,272,057).

Furthermore, the sequences of the present invention can be used to provide an alternative technique for determining the actual base-by-base DNA sequence of selected portions of an individual's genome. Thus, the ATPase-like sequences of the invention can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The ATPase-like sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. The noncoding sequences of SEQ ID NO:1 can comfortably provide positive individual identification with a panel of perhaps 10 to 1,000 primers that each yield a noncoding amplified sequence of 100 bases. If a predicted coding sequence, such as that in SEQ ID NO:2, is used, a more appropriate number of primers for positive individual identification would be 500 to 2,000.

3. Use of Partial ATPase-like Sequences in Forensic Biology

DNA-based identification techniques can also be used in forensic biology. In this manner, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" that is unique to a particular individual. As mentioned above, actual base sequence information can be used for identification as an accurate alternative to patterns formed by restriction enzyme generated fragments. Sequences targeted to noncoding regions of SEQ ID NO:1 are particularly appropriate for this use as greater numbers of polymorphisms occur in the noncoding regions, making it easier to differentiate individuals using this technique. Examples of polynucleotide reagents include the ATPase-like sequences or portions thereof, e.g., fragments derived from the noncoding regions of SEQ ID NO:1 having a length of at least 20 or 30 bases.

The ATPase-like sequences described herein can further be used to provide polynucleotide reagents, e.g., labeled or labelable probes that can be used in, for example, an in situ hybridization technique, to identify a specific tissue. This can be very useful in cases where a forensic pathologist is presented with a tissue of unknown origin. Panels of such ATPase-like probes, can be used to identify tissue by species and/or by organ type.

In a similar fashion, these reagents, e.g., ATPase-like primers or probes can be used to screen tissue culture for contamination (i.e., screen for the presence of a mixture of different types of cells in a culture).

C. Predictive Medicine

The present invention also pertains to the field of predictive medicine in which diagnostic assays, prognostic assays, pharmacogenomics, and monitoring clinical trails are used for prognostic (predictive) purposes to thereby treat an individual prophylactically. These applications are described in the subsections below.

1. Diagnostic Assays

One aspect of the present invention relates to diagnostic assays for detecting ATPase-like protein and/or nucleic acid expression as well as ATPase-like activity, in the context of a biological sample. An exemplary method for detecting the presence or absence of ATPase-like proteins in a biological sample involves obtaining a biological sample from a test subject and contacting the biological sample with a compound or an agent capable of detecting ATPase-like protein or nucleic acid (e.g., mRNA, genomic DNA) that encodes ATPase-like protein such that the presence of ATPase-like protein is detected in the biological sample. Results obtained with a biological sample from the test subject may be compared to results obtained with a biological sample from a control subject.

"Misexpression or aberrant expression", as used herein, refers to a non-wild type pattern of gene expression, at the RNA or protein level. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

A preferred agent for detecting ATPase-like mRNA or genomic DNA is a labeled nucleic acid probe capable of hybridizing to ATPase-like mRNA or genomic DNA. The nucleic acid probe can be, for example, a full-length ATPase-like nucleic acid, such as the nucleic acid of SEQ ID NOS:1, 3, or a portion thereof, such as a nucleic acid molecule of at least 15, 30, 50, 100, 250, or 500 nucleotides in length and sufficient to specifically hybridize under stringent conditions to ATPase-like mRNA or genomic DNA. Other suitable probes for use in the diagnostic assays of the invention are described herein.

A preferred agent for detecting ATPase-like protein is an antibody capable of binding to ATPase-like protein, preferably an antibody with a detectable label. Antibodies can be polyclonal, or more preferably, monoclonal. An intact antibody, or a fragment thereof (e.g., Fab or F(ab')$_2$)can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

The term "biological sample" is intended to include tissues, cells, and biological fluids isolated from a subject, as well as tissues, cells, and fluids present within a subject. That is, the detection method of the invention can be used to detect ATPase-like mRNA, protein, or genomic DNA in a biological sample in vitro as well as in vivo. For example, in vitro techniques for detection of ATPase-like mRNA include Northern hybridizations and in situ hybridizations. In vitro techniques for detection of ATPase-like protein include enzyme linked immunosorbent assays (ELISAs), Western blots, immunoprecipitations, and immunofluorescence. In vitro techniques for detection of ATPase-like genomic DNA include Southern hybridizations. Furthermore, in vivo techniques for detection of ATPase-like protein include introducing into a subject a labeled anti-ATPase-like antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject.

The invention also encompasses kits for detecting the presence of ATPase-like proteins in a biological sample (a test sample). Such kits can be used to determine if a subject is suffering from or is at increased risk of developing a disorder associated with aberrant expression of ATPase-like protein. For example, the kit can comprise a labeled compound or agent capable of detecting ATPase-like protein or mRNA in a biological sample and means for determining the amount of an ATPase-like protein in the sample (e.g., an anti-ATPase-like antibody or an oligonucleotide probe that binds to DNA encoding an ATPase-like protein, e.g., SEQ ID NOS:1 and 3). Kits can also include instructions for observing that the tested subject is suffering from or is at risk of developing a disorder associated with aberrant expression of ATPase-like sequences if the amount of ATPase-like protein or mRNA is above or below a normal level.

For antibody-based kits, the kit can comprise, for example: (1) a first antibody (e.g., attached to a solid support) that binds to ATPase-like protein; and, optionally, (2) a second, different antibody that binds to ATPase-like protein or the first antibody and is conjugated to a detectable agent. For ohigonucleotide-based kits, the kit can comprise, for example: (1) an oligonucleotide, e.g., a detectably labeled oligonucleotide, that hybridizes to an ATPase-like nucleic acid sequence or (2) a pair of primers useful for amplifying an ATPase-like nucleic acid molecule.

The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples that can be assayed and compared to the test sample contained. Each component of the kit is usually enclosed within an individual container, and all of the various containers are within a single package along with instructions for observing whether the tested subject is suffering from or is at risk of developing a disorder associated with aberrant expression of ATPase-like proteins.

2. Other Diagnostic Assays

In another aspect, the invention features, a method of analyzing a plurality of capture probes. The method can be used, e.g., to analyze gene expression. The method includes: providing a two dimensional array having a plurality of addresses, each address of the plurality being positionally distinguishable from each other address of the plurality, and each address of the plurality having a unique capture probe, e.g., a nucleic acid or peptide sequence; contacting the array with an ATPase-like, preferably purified, nucleic acid, preferably purified, polypeptide, preferably purified, or antibody, and thereby evaluating the plurality of capture probes. Binding, e.g., in the case of a nucleic acid, hybridization with a capture probe at an address of the plurality, is detected, e.g., by signal generated from a label attached to the ATPase-like nucleic acid, polypeptide, or antibody.

The capture probes can be a set of nucleic acids from a selected sample, e.g., a sample of nucleic acids derived from a control or non-stimulated tissue or cell.

The method can include contacting the ATPase-like nucleic acid, polypeptide, or antibody with a first array having a plurality of capture probes and a second array having a different plurality of capture probes. The results of each hybridization can be compared, e.g., to analyze differences in expression between a first and second sample. The first plurality of capture probes can be from a control sample, e.g., a wild type, normal, or non-diseased, non-stimulated, sample, e.g., a biological fluid, tissue, or cell sample. The second plurality of capture probes can be from an experimental sample, e.g., a mutant type, at risk, disease-state or disorder-state, or stimulated, sample, e.g., a biological fluid, tissue, or cell sample.

The plurality of capture probes can be a plurality of nucleic acid probes each of which specifically hybridizes, with an allele of ATPase-like. Such methods can be used to diagnose a subject, e.g., to evaluate risk for a disease or disorder, to evaluate suitability of a selected treatment for a subject, to evaluate whether a subject has a disease or disorder.

The method can be used to detect SNPs, as described above.

In another aspect, the invention features, a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express ATPase-like or from a cell or subject in which an ATPase-like mediated response has been elicited, e.g., by contact of the cell with ATPase-like nucleic acid or protein, or administration to the cell or subject ATPase-like nucleic acid or protein; contacting the array with one or more inquiry probe, wherein an inquiry probe can be a nucleic acid, polypeptide, or antibody (which is preferably other than ATPase-like nucleic acid, polypeptide, or antibody); providing a two dimensional array having a plurality of addresses, each address of the plurality being positionally distinguishable from each other address of the plurality, and each address of the plurality having a unique capture probe, e.g., wherein the capture probes are from a cell or subject which does not express ATPase-like (or does not express as highly as in the case of the ATPase-like positive plurality of capture probes) or from a cell or subject which in which an ATPase-like mediated response has not been elicited (or has been elicited to a lesser extent than in the first sample); contacting the array with one or more inquiry probes (which is preferably other than an ATPase-like nucleic acid, polypeptide, or antibody), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody.

In another aspect, the invention features, a method of analyzing ATPase-like, e.g., analyzing structure, function, or relatedness to other nucleic acid or amino acid sequences. The method includes: providing an ATPase-like nucleic acid or amino acid sequence, e.g., a nucleotide sequence from 300–1916 or a portion thereof; comparing the ATPase-like sequence with one or more preferably a plurality of sequences from a collection of sequences, e.g., a nucleic acid or protein sequence database; to thereby analyze ATPase-like.

The method can include evaluating the sequence identity between an ATPase-like sequence and a database sequence. The method can be performed by accessing the database at a second site, e.g., over the internet.

In another aspect, the invention features, a set of oligonucleotides, useful, e.g., for identifying SNP's, or identifying specific alleles of an ATPase-like gene. The set includes a plurality of oligonucleotides, each of which has a different nucleotide at an interrogation position, e.g., an SNP or the site of a mutation. In a preferred embodiment, the oligonucleotides of the plurality identical in sequence with one another (except for differences in length). The oligonucleotides can be provided with differential labels, such that an oligonucleotides which hybridizes to one allele provides a signal that is distinguishable from an oligonucleotides which hybridizes to a second allele.

3. Prognostic Assays

The methods described herein can furthermore be utilized as diagnostic or prognostic assays to identify subjects having or at risk of developing a disease or disorder associated with ATPase-like protein, ATPase-like nucleic acid expression, or ATPase-like activity. Prognostic assays can be used for prognostic or predictive purposes to thereby prophylactically treat an individual prior to the onset of a disorder characterized by or associated with ATPase-like protein, ATPase-like nucleic acid expression, or ATPase-like activity.

Thus, the present invention provides a method in which a test sample is obtained from a subject, and ATPase-like protein or nucleic acid (e.g., mRNA, genomic DNA) is detected, wherein the presence of ATPase-like protein or nucleic acid is diagnostic for a subject having or at risk of developing a disease or disorder associated with aberrant ATPase-like expression or activity. As used herein, a "test sample" refers to a biological sample obtained from a subject of interest. For example, a test sample can be a biological fluid (e.g., serum), cell sample, or tissue.

Furthermore, using the prognostic assays described herein, the present invention provides methods for determining whether a subject can be administered a specific agent (e.g., an agonist, antagonist, peptidomimetic, protein, peptide, nucleic acid, small molecule, or other drug candidate) or class of agents (e.g., agents of a type that decrease ATPase-like activity) to effectively treat a disease or disorder associated with aberrant ATPase-like expression or activity. In this manner, a test sample is obtained and ATPase-like protein or nucleic acid is detected. The presence of ATPase-like protein or nucleic acid is diagnostic for a subject that can be administered the agent to treat a disorder associated with aberrant ATPase-like expression or activity.

The methods of the invention can also be used to detect genetic lesions or mutations in an ATPase-like gene, thereby determining if a subject with the lesioned gene is at risk for a disorder characterized by aberrant cellular processes including, altered protein sorting, altered gene expression, altered cell division, altered protein stability, etc. In preferred embodiments, the methods include detecting, in a sample of cells from the subject, the presence or absence of a genetic lesion or mutation characterized by at least one of an alteration affecting the integrity of a gene encoding an ATPase-like-protein, or the misexpression of the ATPase-like gene. For example, such genetic lesions or mutations can be detected by ascertaining the existence of at least one of: (1) a deletion of one or more nucleotides from an ATPase-like gene; (2) an addition of one or more nucleotides to an ATPase-like gene; (3) a substitution of one or more nucleotides of an ATPase-like gene; (4) a chromosomal rearrangement of an ATPase-like gene; (5) an alteration in the level of a messenger RNA transcript of an ATPase-like gene; (6) an aberrant modification of an ATPase-like gene, such as of the methylation pattern of the genomic DNA; (7) the presence of a non-wild-type splicing pattern of a messenger RNA transcript of an ATPase gene; (8) a non-wild-type level of an ATPase-like-protein; (9) an allelic loss of an ATPase-like gene; and (10) an inappropriate post-translational modification of an ATPase-like-protein. As described herein, there are a large number of assay techniques known in the art that can be used for detecting lesions in an ATPase-like gene. Any cell type or tissue in which ATPase-like proteins are expressed may be utilized in the prognostic assays described herein.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in the ATPase-like-gene (see, e.g., Abravaya et al. (1995) *Nucleic Acids Res.* 23:675–682). It is anticipated that PCR and/or LCR may be desirable to use as a preliminary amplification step in conjunction with any of the techniques used for detecting mutations described herein.

Alternative amplification methods include self sustained sequence replication (Guatelli et al. (1990) *Proc. Natl. Acad. Sci. USA* 87:1874–1878), transcriptional amplification system (Kwoh et al. (1989) *Proc. Natl. Acad. Sci. USA* 86:1173–1177), Q-Beta Replicase (Lizardi et al. (1988) *Bio/Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in an ATPase-like gene from a sample cell can be identified by alterations in restriction enzyme cleavage patterns of isolated test sample and control DNA digested with one or more restriction endonucleases. Moreover, the use of sequence specific ribozymes (see, e.g., U.S. Pat. No. 5,498,531) can be used to score for the presence of specific mutations by development or loss of a ribozyme cleavage site.

In other embodiments, genetic mutations in an ATPase-like molecule can be identified by hybridizing a sample and control nucleic acids, e.g., DNA or RNA, to high density arrays containing hundreds or thousands of oligonucleotides probes (Cronin et al. (1996) *Human Mutation* 7:244–255; Kozal et al. (1996) *Nature Medicine* 2:753–759). In yet another embodiment, any of a variety of sequencing reactions known in the art can be used to directly sequence the ATPase-like gene and detect mutations by comparing the sequence of the sample ATPase-like gene with the corresponding wild-type (control) sequence. Examples of sequencing reactions include those based on techniques developed by Maxim and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Bio/Techniques* 19:448), including sequencing by mass spectrometry (see, e.g., PCT Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the ATPase-like gene include methods in which protection from cleavage agents is used to detect mismatched bases in RNA/RNA or RNA/DNA heteroduplexes (Myers et al. (1985) *Science* 230:1242). See, also Cotton et al. (1988) *Proc. Natl. Acad. Sci. USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more "DNA mismatch repair" enzymes that recognize mismatched base pairs in double-stranded DNA in defined systems for detecting and mapping point mutations in ATPase-like cDNAs obtained from samples of cells. See, e.g., Hsu et al. (1994) *Carcinogenesis* 15:1657–1662. According to an exemplary embodiment, a probe based on an ATPase-like sequence, e.g., a wild-type ATPase-like sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in ATPase-like genes. For example, single-strand conformation polymorphism (SSCP) may be used to detect differences in electrophoretic mobility between mutant and wild-type nucleic acids (Orita et al. (1989) *Proc. Natl. Acad. Sci. USA* 86:2766; see also Cotton (1993) *Mutat. Res.* 285:125–144; Hayashi (1992) *Genet. Anal. Tech. Appl.* 9:73–79). The sensitivity of the assay may be enhanced by using RNA (rather than DNA), in which the secondary structure is more sensitive to a change in sequence. In a preferred embodiment, the subject method utilizes heteroduplex analysis to separate double-stranded heteroduplex molecules on the basis of changes in electrophoretic mobility (Keen et al. (1991) *Trends Genet.* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions that permit hybridization only if a perfect match is found (Saiki et al. (1986) *Nature* 324:163); Saiki et al. (1989) *Proc. Natl. Acad. Sci. USA* 86:6230). Such allele-specific oligonucleotides are hybridized to PCR-amplified target DNA or a number of different mutations when the oligonucleotides are attached to the hybridizing membrane and hybridized with labeled target DNA.

Alternatively, allele-specific amplification technology, which depends on selective PCR amplification, may be used in conjunction with the instant invention. Oligonucleotides used as primers for specific amplification may carry the mutation of interest in the center of the molecule so that amplification depends on differential hybridization (Gibbs et al. (1989) *Nucleic Acids Res.* 17:2437–2448) or at the extreme 3' end of one primer where, under appropriate conditions, mismatch can prevent or reduce polymerase extension (Prossner (1993) *Tibtech* 11:238). In addition, it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci. USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing prepackaged diagnostic kits comprising at least one probe nucleic acid or antibody reagent described herein, which may be conveniently used, e.g., in clinical settings to diagnosed patients exhibiting symptoms or family history of a disease or illness involving an ATPase-like gene.

4. Pharmacogenomics

Agents, or modulators that have a stimulatory or inhibitory effect on ATPase-like activity (e.g., ATPase-like gene expression) as identified by a screening assay described herein, can be administered to individuals to treat (prophylactically or therapeutically) disorders associated with aberrant ATPase-like activity as well as to modulate a cellular phenotype associated with aberrant ATPase-like activity. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of ATPase-like protein, expression of ATPase-like nucleic acid, or mutation content of ATPase-like genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) *Clin. Chem.* 43(2): 254–266. In general, two types of pharmacogenetic conditions can be differentiated. Genetic conditions transmitted as a single factor altering the way drugs act on the body are referred to as "altered drug action." Genetic conditions transmitted as single factors altering the way the body acts on drugs are referred to as "altered drug metabolism". These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (antimalarials, sulfonamides, analgesics, nitrofurans) and consumption of fava beans.

Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a ATPase-like molecule or ATPase-like modulator as well as tailoring the dosage and/or therapeutic regimen of treatment with a ATPase-like molecule or ATPase-like modulator.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drug's target is known (e.g., an ATPase-like protein of the present invention), all common variants of that gene can be fairly easily identified in the population and it can be determined if having one version of the gene versus another is associated with a particular drug response.

Alternatively, a method termed the "gene expression profiling", can be utilized to identify genes that predict drug response. For example, the gene expression of an animal dosed with a drug (e.g., an ATPase-like molecule or ATPase-like modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with an ATPase-like molecule or ATPase-like modulator, such as a modulator identified by one of the exemplary screening assays described herein.

The present invention further provides methods for identifying new agents, or combinations, that are based on identifing agents that modulate the activity of one or more of the gene products encoded by one or more of the ATPase-like genes of the present invention, wherein these products may be associated with resistance of the cells to a therapeutic agent. Specifically, the activity of the proteins encoded by the ATPase-like genes of the present invention can be used as a basis for identifying agents for overcoming agent resistance. By blocking the activity of one or more of the resistance proteins, target cells will become sensitive to treatment with an agent that the unmodified target cells were resistant to.

Monitoring the influence of agents (e.g., drugs) on the expression or activity of a ATPase-like protein can be applied in clinical trials. For example, the effectiveness of an agent determined by a screening assay as described herein to increase ATPase-like gene expression, protein levels, or upregulate ATPase-like activity, can be monitored in clinical trials of subjects exhibiting decreased ATPase-like gene expression, protein levels, or downregulated ATPase-like activity. Alternatively, the effectiveness of an agent determined by a screening assay to decrease ATPase-like gene expression, protein levels, or downregulate ATPase-like activity, can be monitored in clinical trials of subjects exhibiting increased ATPase-like gene expression, protein levels, or upregulated ATPase-like activity. In such clinical trials, the expression or activity of a ATPase-like gene, and preferably, other genes that have been implicated in, for example, a ATPase-like-associated disorder can be used as a "read out" or markers of the phenotype of a particular cell.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, a PM will show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of ATPase-like protein, expression of ATPase-like nucleic acid, or mutation content of ATPase-like genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with an ATPase-like modulator, such as a modulator identified by one of the exemplary screening assays described herein.

5. Monitoring of Effects During Clinical Trials

Monitoring the influence of agents (e.g., drugs, compounds) on the expression or activity of ATPase-like genes can be applied not only in basic drug screening but also in clinical trials. For example, the effectiveness of an agent, as determined by a screening assay as described herein, to increase or decrease ATPase-like gene expression, protein levels, or protein activity, can be monitored in clinical trials of subjects exhibiting decreased or increased ATPase-like gene expression, protein levels, or protein activity. In such clinical trials, ATPase-like expression or activity and preferably that of other genes that have been implicated in influencing ATPase-like expression or activity, can be used as a marker of the immune responsiveness of a particular cell.

For example, and not by way of limitation, genes that are modulated in cells by treatment with an agent (e.g., compound, drug, or small molecule) that modulates ATPase-like activity (e.g., as identified in a screening assay described herein) can be identified. Thus, to study the effect of agents on cellular disorders resulting from aberrant ATPase-like activity, for example, in a clinical trial, cells can be isolated and RNA prepared and analyzed for the levels of expression of ATPase-like genes and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of ATPase-like genes or other genes. In this way, the gene expression pattern can serve as a marker, indicative of the physiological response of the cells to the agent. Accordingly, this response state may be determined before, and at various points during, treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (1) obtaining a preadministration sample from a subject prior to administration of the agent; (2) detecting the level of expression of an ATPase-like protein, mRNA, or genomic DNA in the preadministration sample; (3) obtaining one or more postadministration samples from the subject; (4) detecting the level of expression or activity of the ATPase-like protein, mRNA, or genomic DNA in the postadministration samples; (5) comparing the level of expression or activity of the ATPase-like protein, mRNA, or genomic DNA in the preadministration sample with the ATPase-like protein, mRNA, or genomic DNA in the postadministration sample or samples; and (vi) altering the administration of the agent to the subject accordingly to bring about the desired effect, i.e., for example, an increase or a decrease in the expression or activity of an ATPase-like protein.

C. Methods of Treatment

The present invention provides for both prophylactic and therapeutic methods of treating a subject at risk of (or susceptible to) a disorder or having a disorder associated with aberrant ATPase-like expression or activity. Additionally, the compositions of the invention find use in the treatment of disorders described herein. Thus, therapies for disorders associated with ATPase-like molecules are encompassed herein. "Subject", as used herein, can refer to a mammal, e.g., a human, or to an experimental or animal or disease model. The subject can also be a non-human animal, e.g., a horse, cow, goat, or other domestic animal.

"Treatment" is herein defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A "therapeutic agent" includes, but is not limited to, small molecules, peptides, antibodies, ribozymes and antisense oligonucleotides.

1. Prophylactic Methods

In one aspect, the invention provides a method for preventing in a subject a disease or condition associated with an aberrant ATPase-like expression or activity by administering to the subject an agent that modulates ATPase-like expression or at least one ATPase-like gene activity. Subjects at risk for a disease that is caused, or contributed to, by aberrant ATPase-like expression or activity can be identified by, for example, any or a combination of diagnostic or prognostic assays as described herein. Administration of a prophylactic agent can occur prior to the manifestation of symptoms characteristic of the ATPase-like aberrancy, such that a disease or disorder is prevented or, alternatively, delayed in its progression. Depending on the type of ATPase-like aberrancy, for example, an ATPase-like agonist or ATPase-like antagonist agent can be used for treating the subject. The appropriate agent can be determined based on screening assays described herein.

2. Therapeutic Methods

Another aspect of the invention pertains to methods of modulating ATPase-like expression or activity for therapeutic purposes. The modulatory method of the invention involves contacting a cell with an agent that modulates one or more of the activities of ATPase-like protein activity associated with the cell. An agent that modulates ATPase-like protein activity can be an agent as described herein, such as a nucleic acid or a protein, a naturally-occurring cognate ligand of an ATPase-like protein, a peptide, an ATPase-like peptidomimetic, or other small molecule. In one embodiment, the agent stimulates one or more of the biological activities of ATPase-like protein. Examples of such stimulatory agents include active ATPase-like protein and a nucleic acid molecule encoding an ATPase-like protein that has been introduced into the cell. In another embodiment, the agent inhibits one or more of the biological activities of ATPase-like protein. Examples of such inhibitory agents include antisense ATPase-like nucleic acid molecules and anti-ATPase-like antibodies.

These modulatory methods can be performed in vitro (e.g., by culturing the cell with the agent) or, alternatively, in vivo (e.g, by administering the agent to a subject). As such, the present invention provides methods of treating an individual afflicted with a disease or disorder characterized by aberrant expression or activity of an ATPase-like protein or nucleic acid molecule. In one embodiment, the method involves administering an agent (e.g., an agent identified by a screening assay described herein), or a combination of agents, that modulates (e.g., upregulates or downregulates) ATPase-like expression or activity. In another embodiment, the method involves administering an ATPase-like protein or nucleic acid molecule as therapy to compensate for reduced or aberrant ATPase-like expression or activity.

Stimulation of ATPase-like activity is desirable in situations in which an ATPase-like protein is abnormally downregulated and/or in which increased ATPase-like activity is likely to have a beneficial effect. Conversely, inhibition of ATPase-like activity is desirable in situations in which ATPase-like activity is abnormally upregulated and/or in which decreased ATPase-like activity is likely to have a beneficial effect.

This invention is further illustrated by the following examples, which should not be construed as limiting.

EXPERIMENTAL

Example 1

Tissue Distribution of ATPase-like mRNA

Northern blot hybridizations with various RNA samples can be performed under standard conditions and washed under stringent conditions, i.e., 0.2×SSC at 65° C. A DNA probe corresponding to all or a portion of the ATPase-like cDNA (SEQ ID NO:1 or 3) can be used. The DNA was radioactively labeled with $^{32}$P-dCTP using the Prime-It Kit (Stratagene, La Jolla, Calif.) according to the instructions of the supplier. Filters containing mRNA from mouse hematopoietic and endocrine tissues, and cancer cell lines (Clontech, Palo Alto, Calif.) can be probed in ExpressHyb hybridization solution (Clontech) and washed at high stringency according to manufacturer's recommendations.

Figure 4:
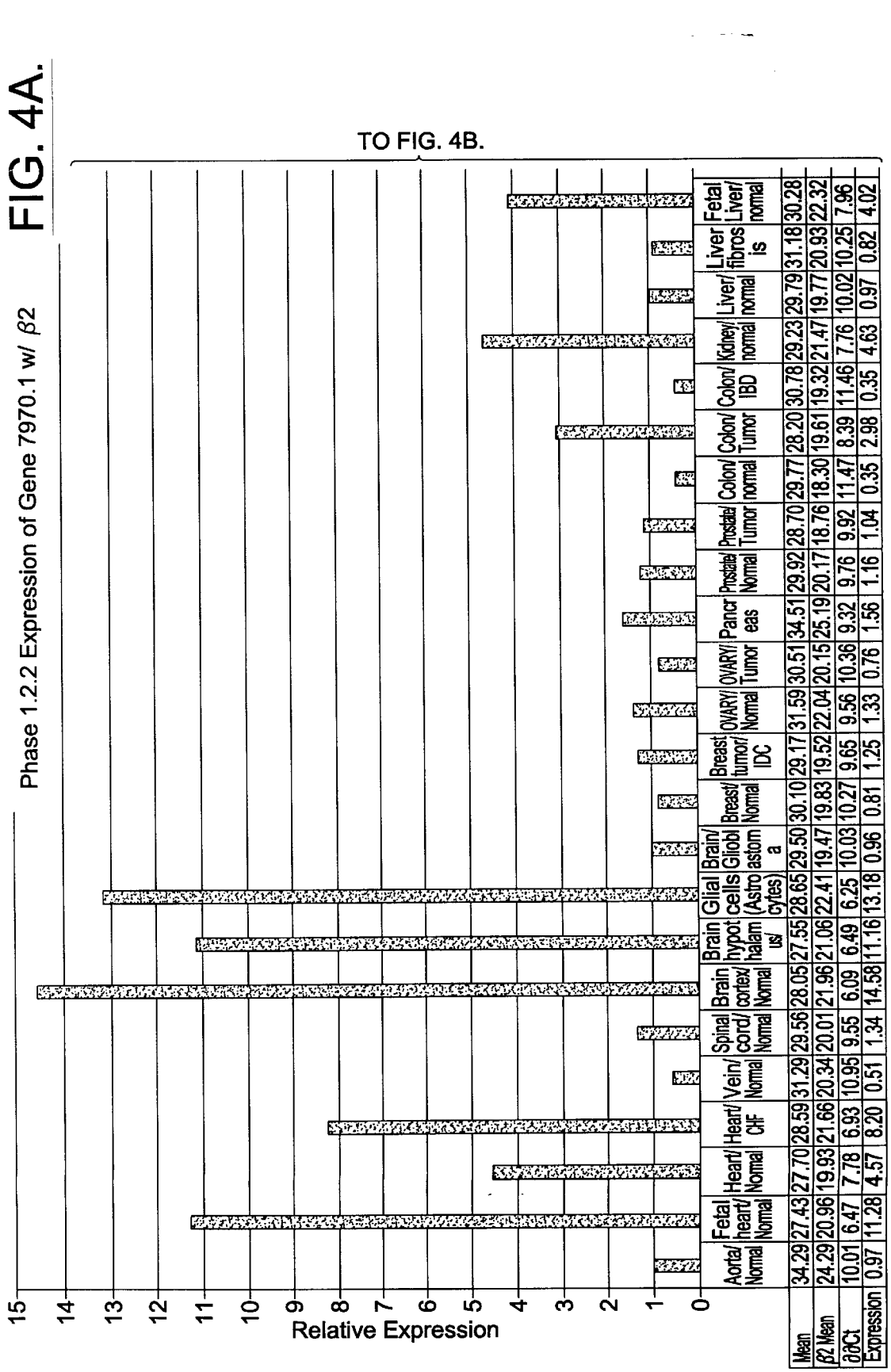
FIGS. 4A and 4B show the expression level of the 7970 mRNA transcript in various tissues and cell lines.
Figure 5:
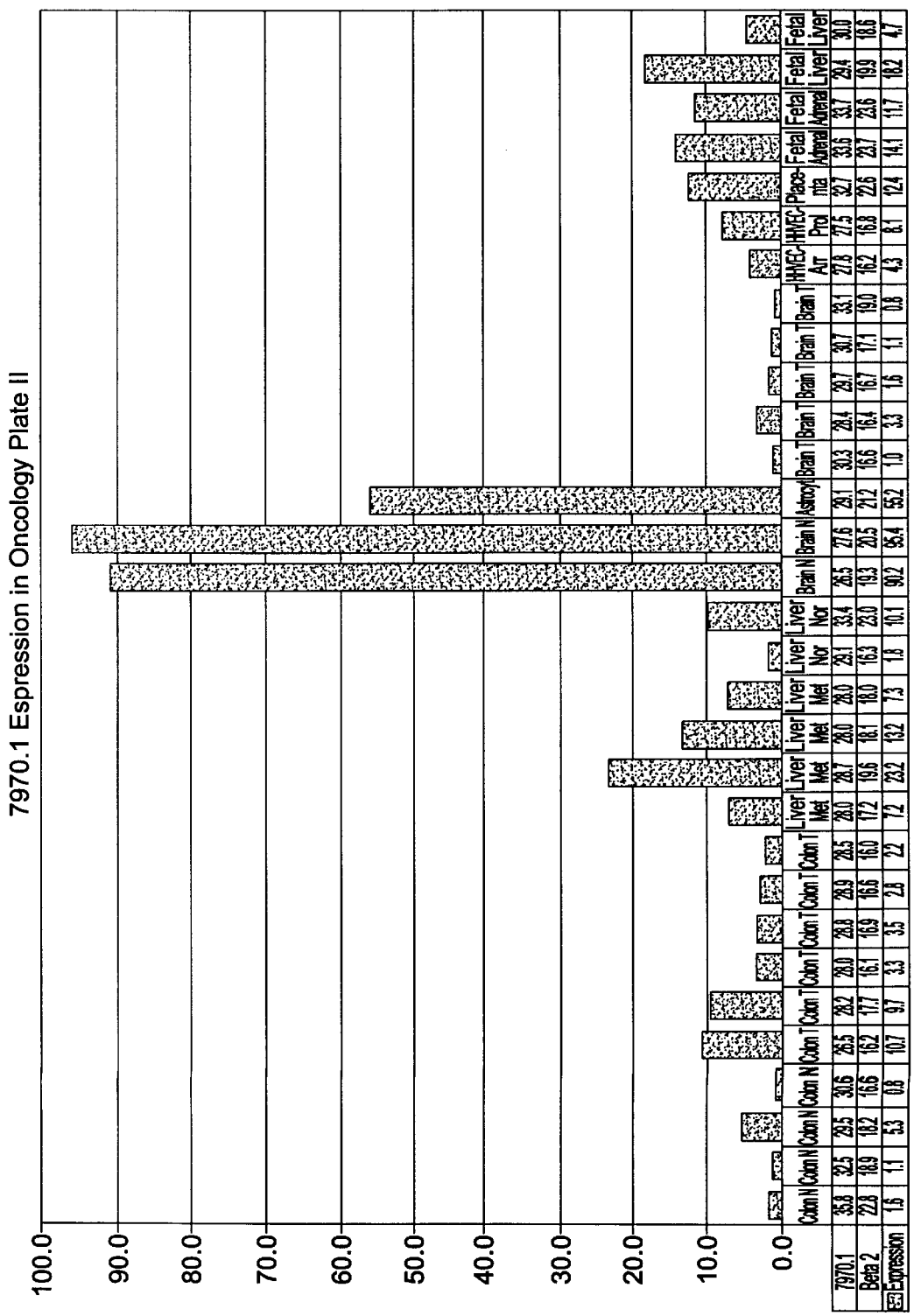
FIG. 5 shows the expression level of the 7970 mRNA transcript in various normal and tumorous tissues and cell lines.
Figure 6A:
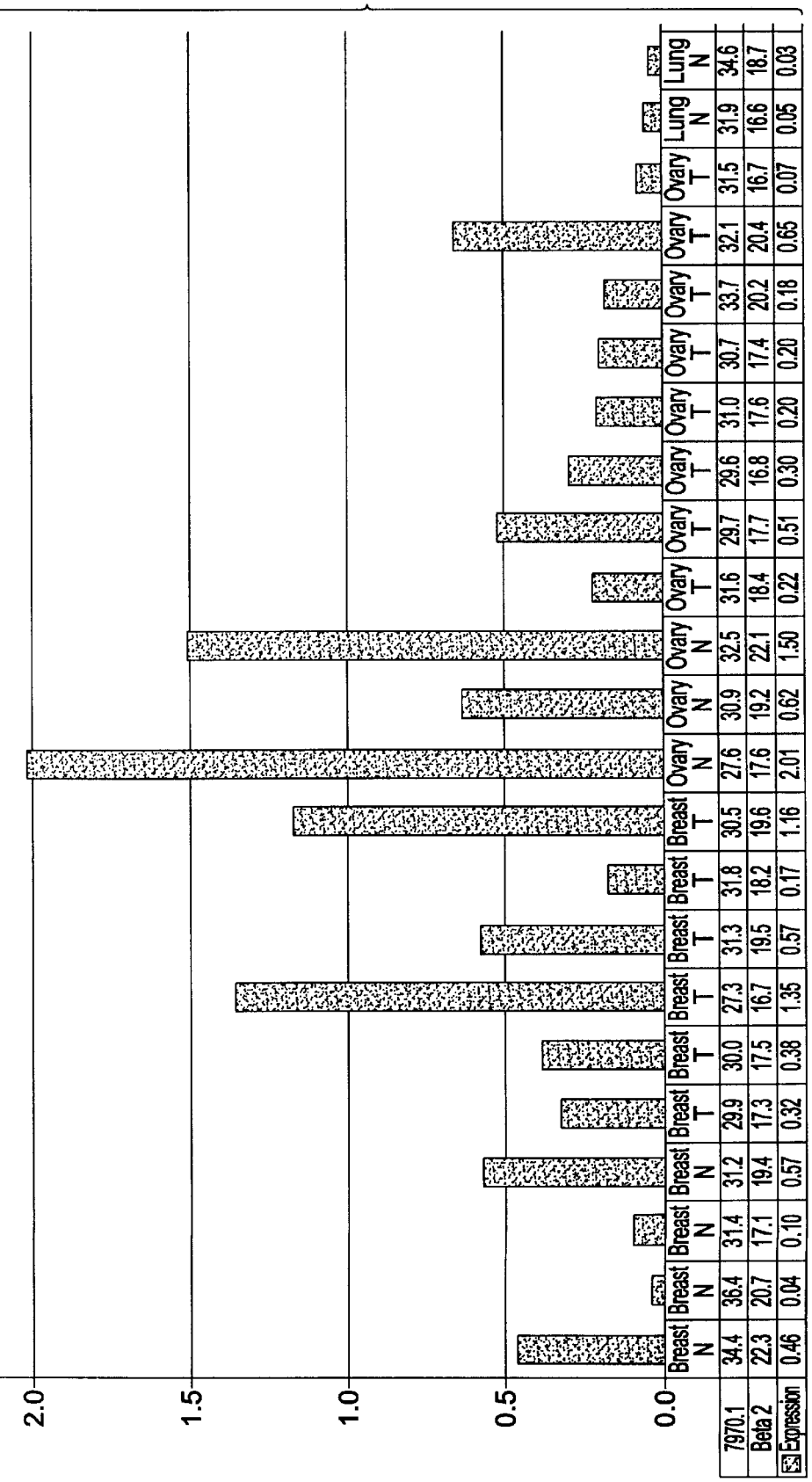
FIGS. 6A and 6B show the expression level of the 7970 mRNA transcript in various normal and tumorous tissues.
Figure 6B:
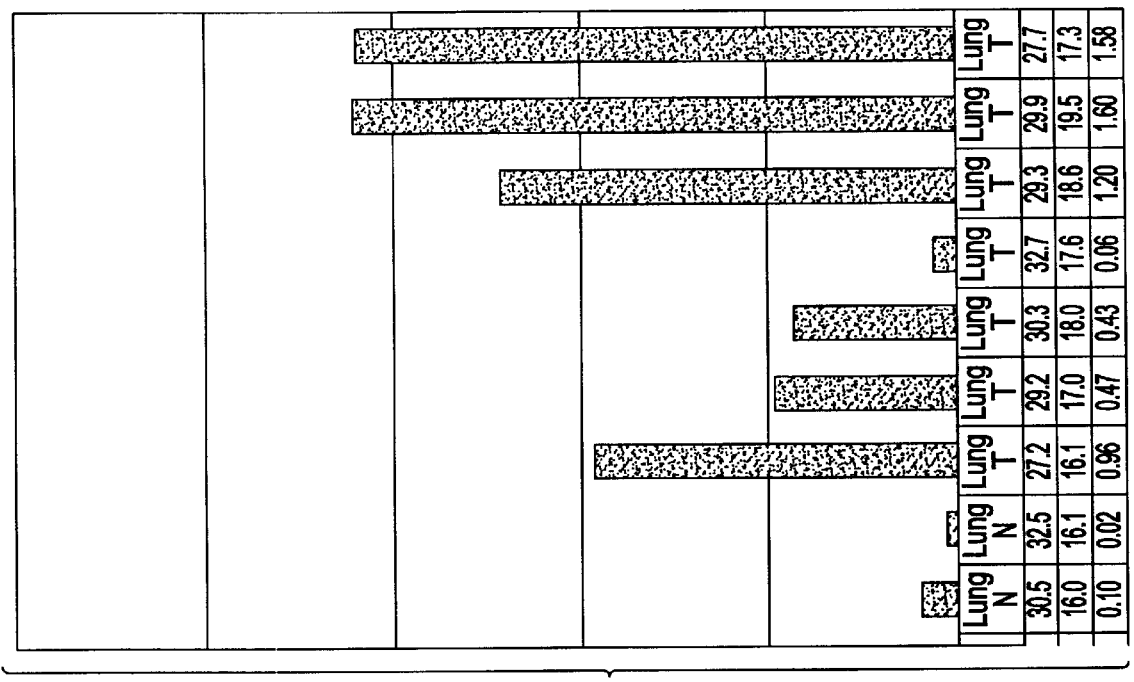
Figure 7:
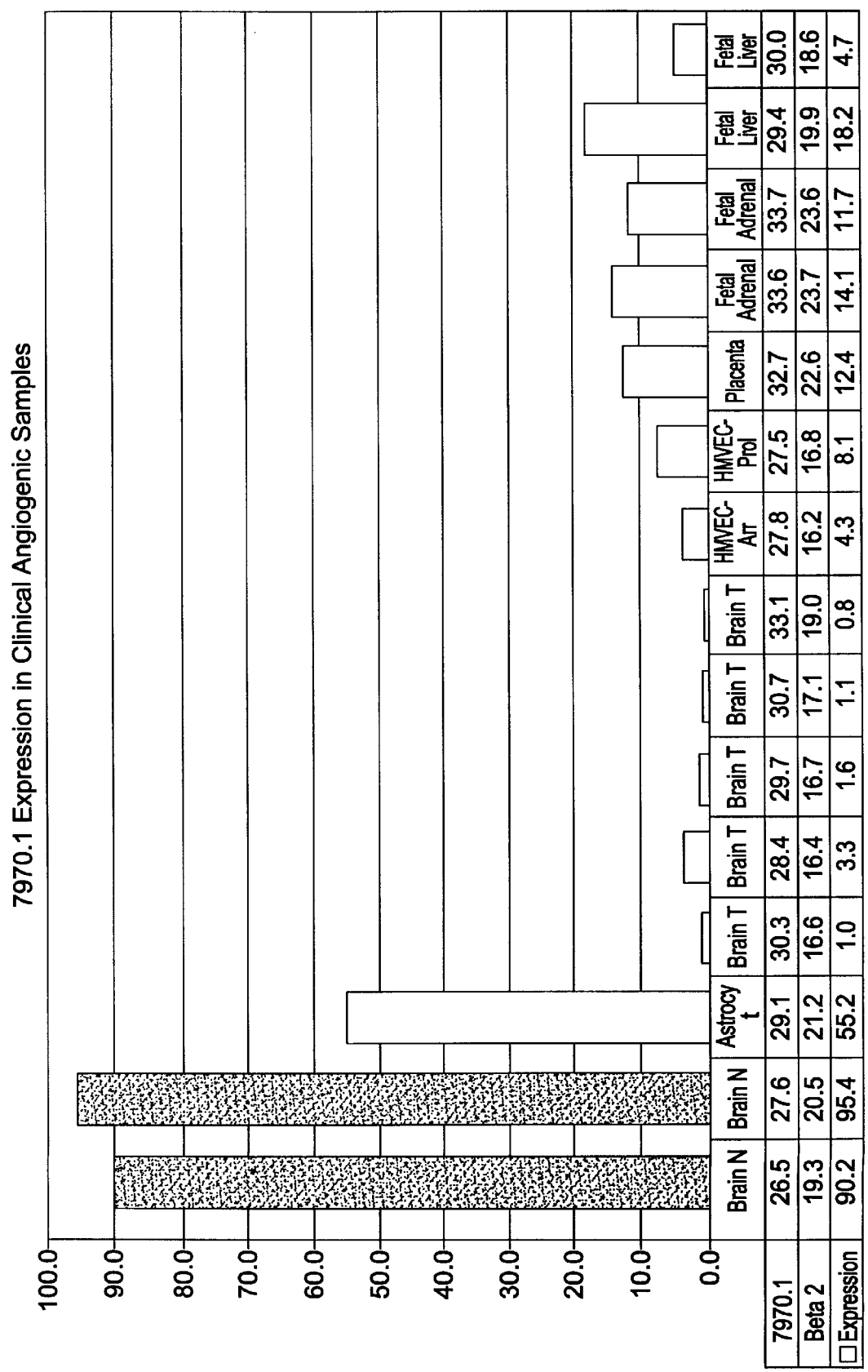
FIG. 7 shows the expression level of the 7970 mRNA transcript in clinical angiogenic samples.
Figure 8:
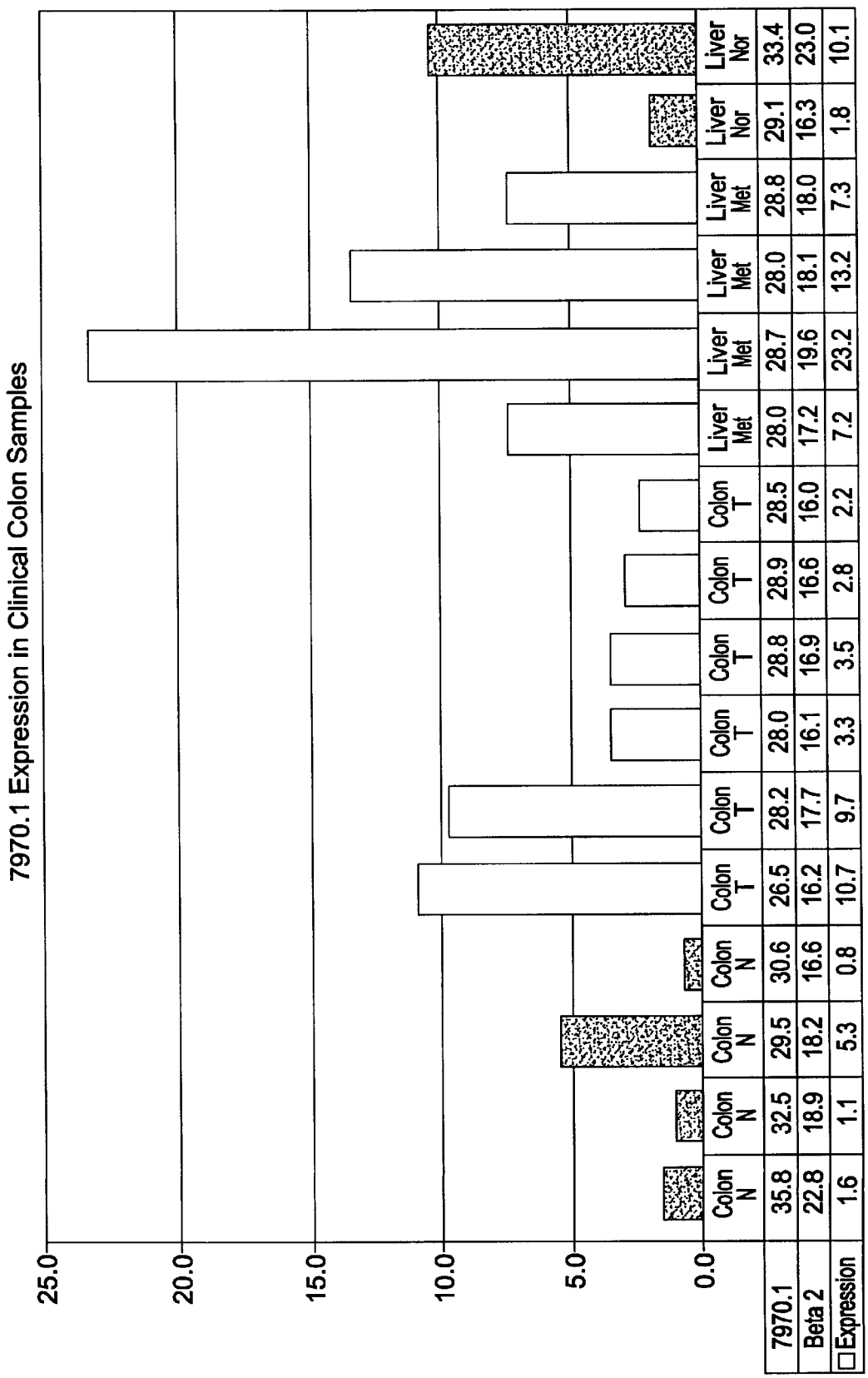
FIG. 8 shows the expression level of the 7970 transcript in clinical colon and liver samples.

TAQMAN analysis of the 7970 sequence revealed expression in a number of tissues as shown in FIG. 4. High levels of 7970 transcripts are seen in the fetal heart, normal heart, heart (CHF), brain cortex, brain hypothalamus, glial cells, and epithelial cells. Moderate levels of expression are found in kidney, fetal liver, aortic SMC early, aortic SMC late, shear HUVEC, and static HUVEC. Low levels of expression were found in the aorta, vein, spinal cord, brain, gioblastoma, breast, ovary, tumorous breast, tumorous ovary, pancreas, prostate, tumorous prostate, colon, tumorous colon, liver, liver fibrosis, lung, tumorous lung, lung (COPD), spleen, tonsil, lymph node, thymus, endothelial cells (aortic), skeletal muscle, fibroblasts, skin, adipose, osteoblasts (primary), osteoblasts (undifferentiated), osteoblasts (differentiated), and osteoclasts.

The expression of the 7970 sequence in various tumorous and normal tissues was also determined. FIGS. 5–8 and FIGS. 10–12 show the relative expression levels of the 7970 transcript in various tissues including, for example, normal and tumorous colon tissues, normal liver and metastatic liver tissues, normal brain and tumorous brain tissues, normal breast and tumorous breast tissues, normal ovary and tumorous ovary tissues, and normal lung and tumorous lung tissues.

Figure 9:
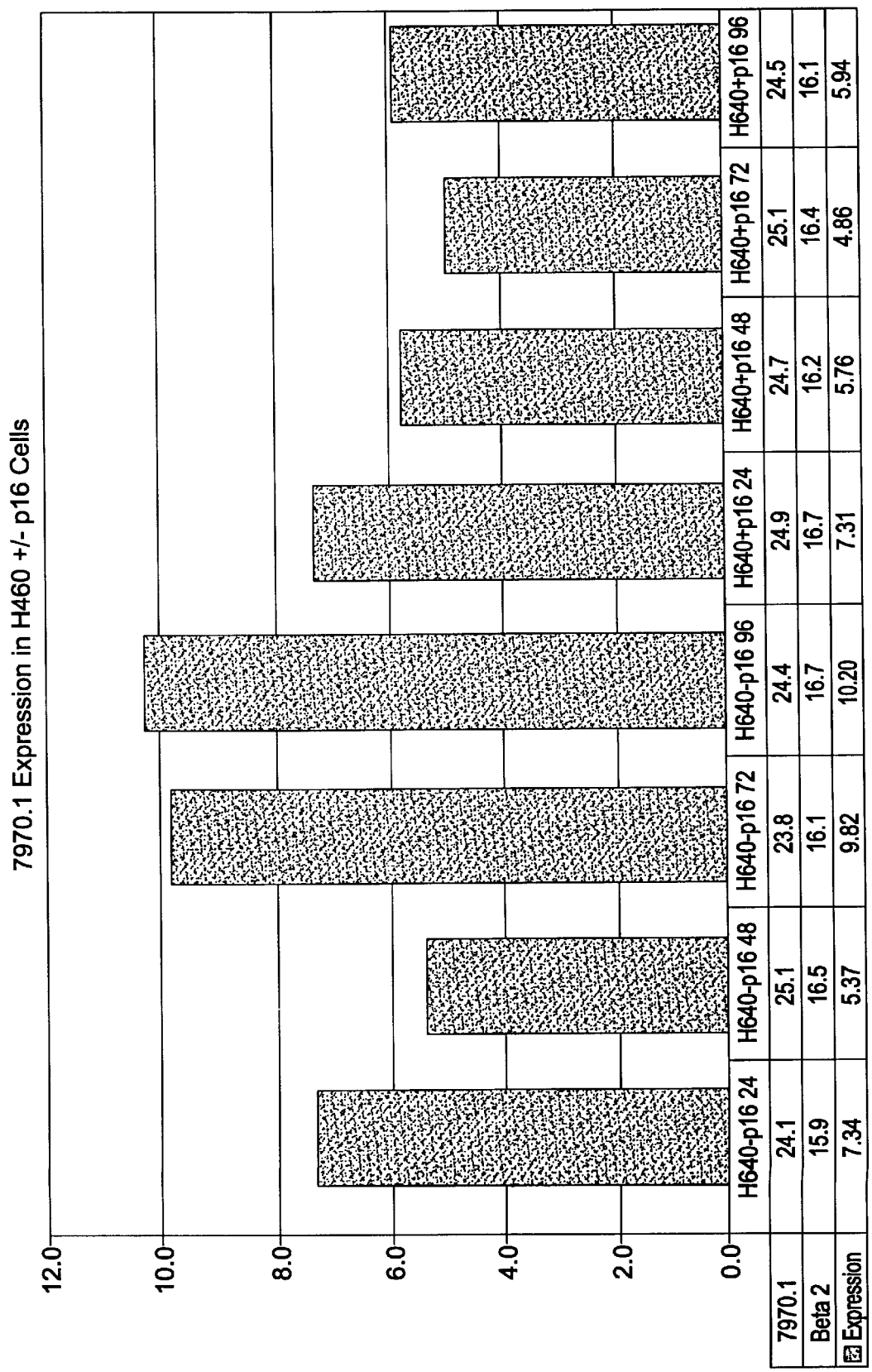
FIG. 9 shows the expression level of the 7970 transcript in a non-small cell lung cancer cell line (H640) in the presence and absence of the p16 gene.
Figure 10:
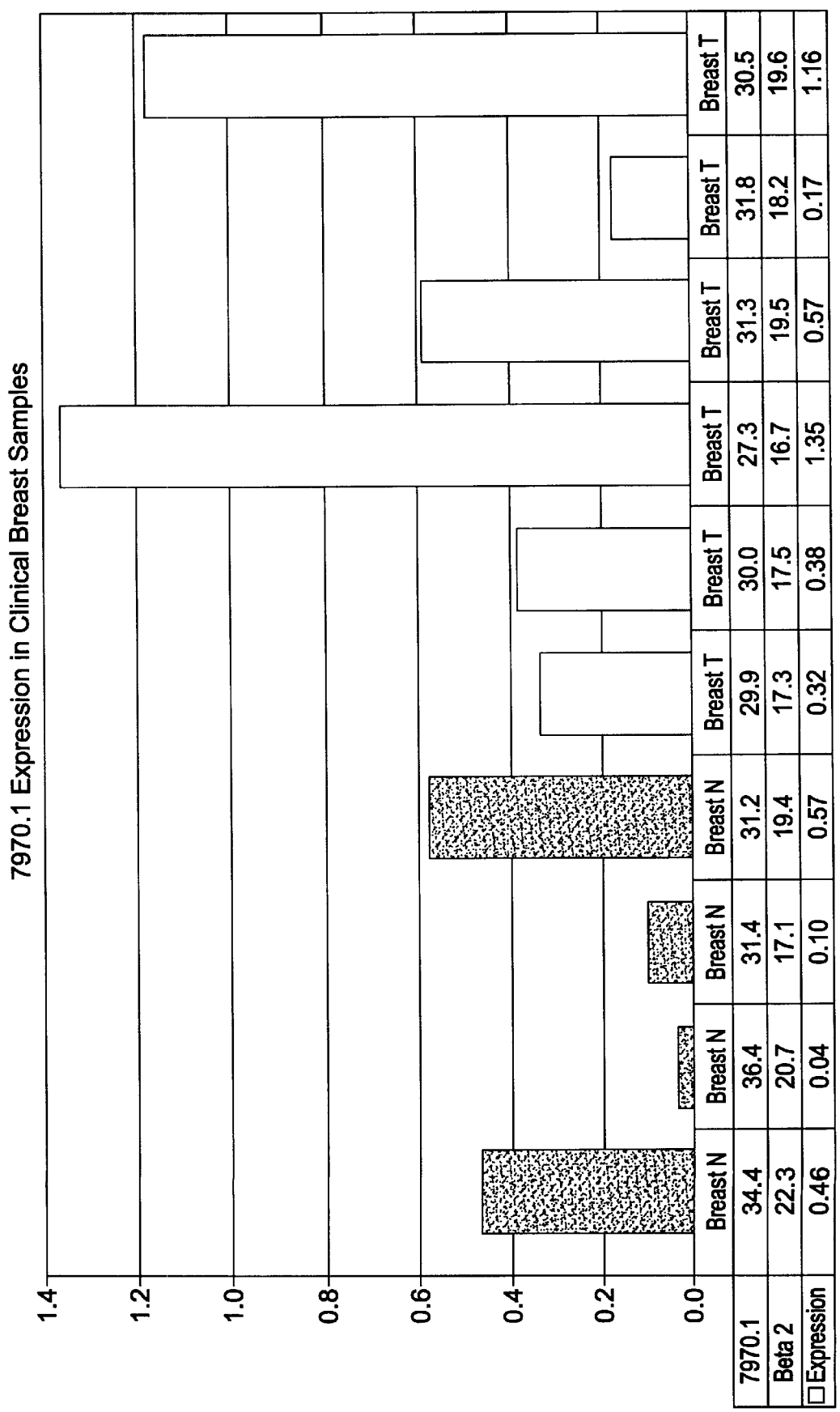
FIG. 10 shows the expression of the 7970 transcript in clinical breast samples.
Figure 11:
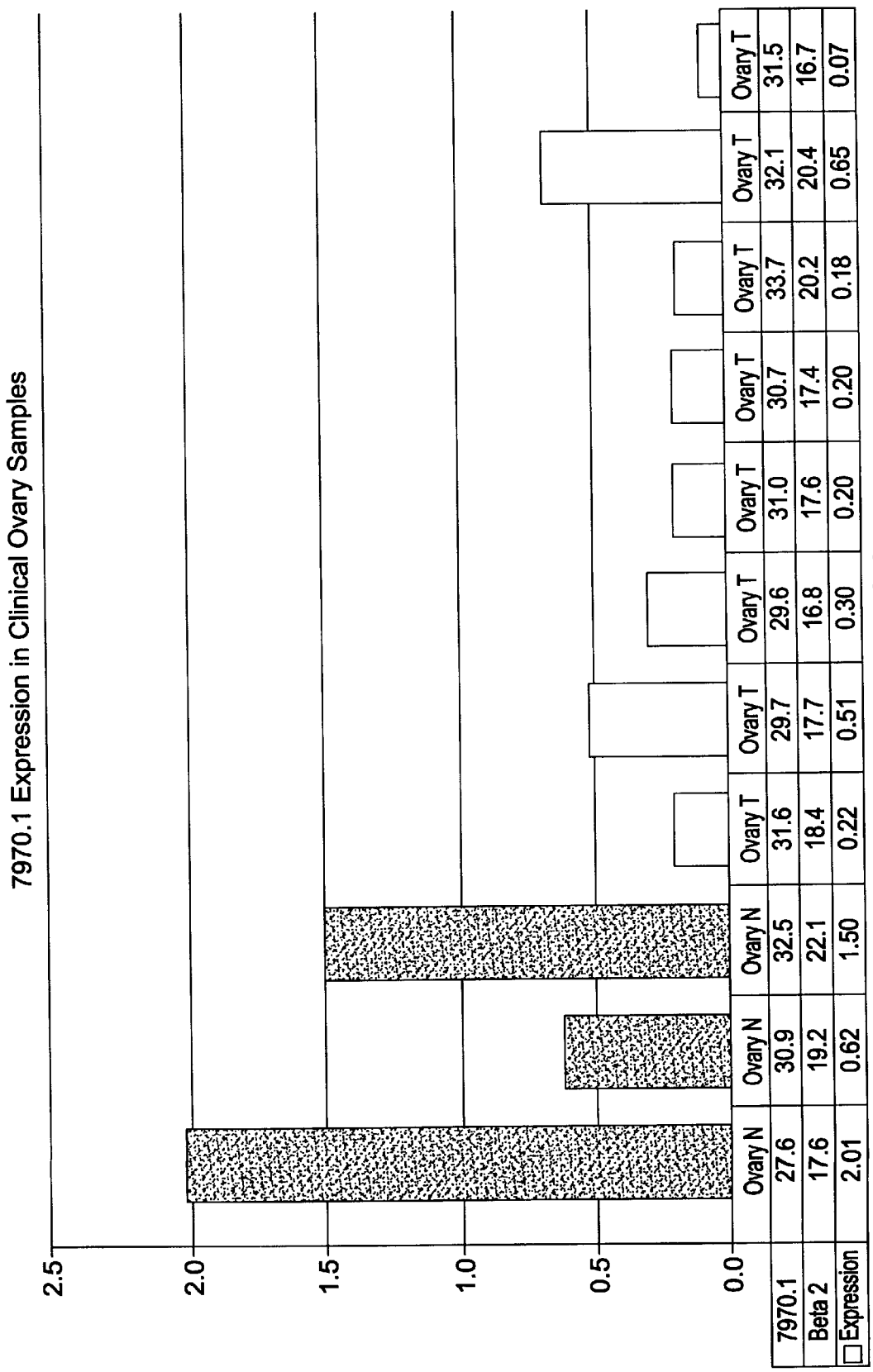
FIG. 11 shows the expression of the 7970 transcript in clinical ovary samples.
Figure 12:
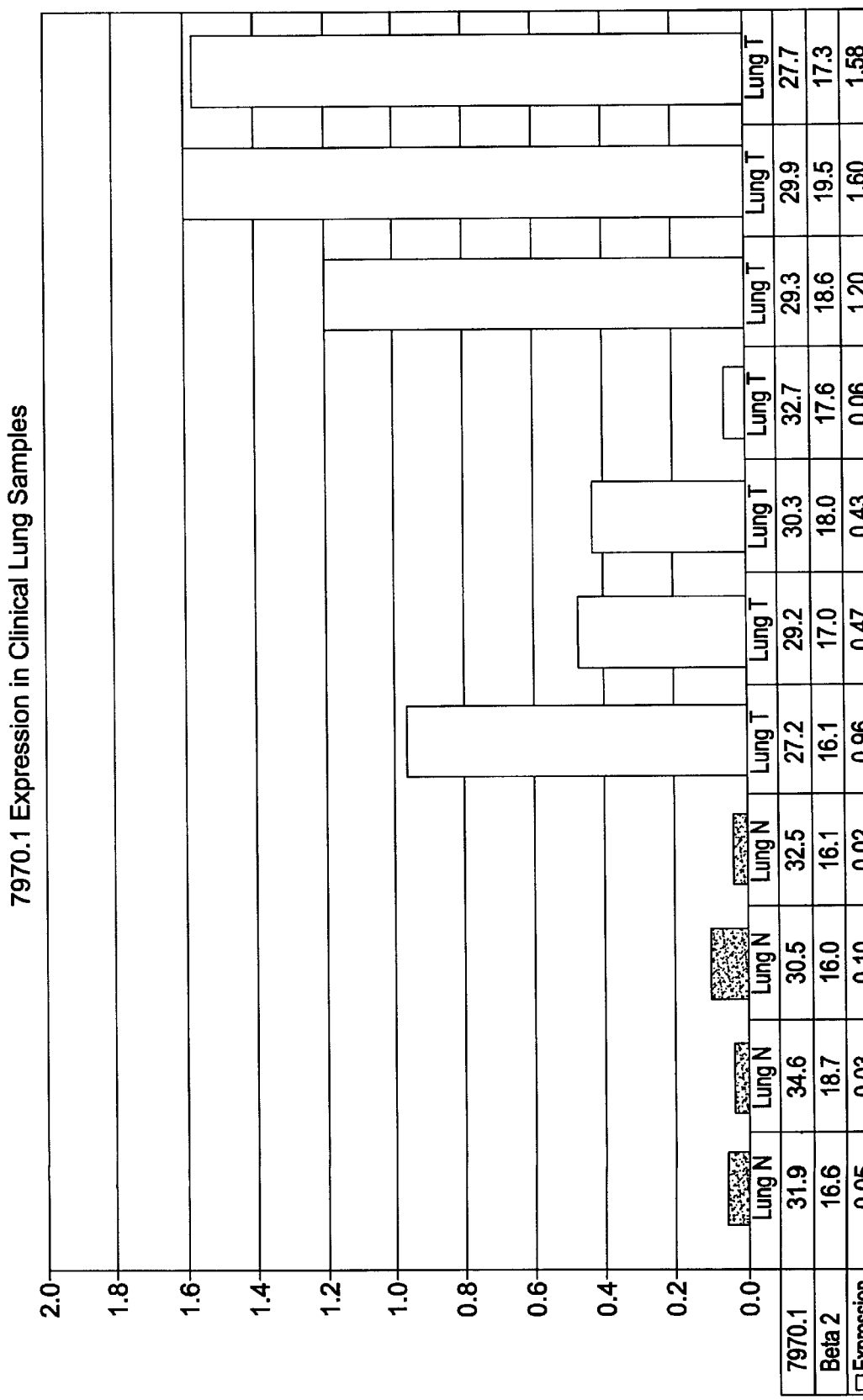
FIG. 12 shows the expression of the 7970 transcript in clinical lung samples.

FIG. 9 further shows the expression level of the 7970 transcript in a non-small cell lung cancer cell line (H640) in the presence and the absence of the p16 gene.

Example 2

Recombinant Expression of ATPase-like in Bacterial Cells

In this example, the ATPase-like sequence is expressed as a recombinant glutathione-S-transferase (GST) fusion polypeptide in *E. coli* and the fusion polypeptide is isolated and characterized. Specifically, the ATPase-like sequence is fused to GST and this fusion polypeptide is expressed in *E. coli*, e.g., strain PEB199. Expression of the GST-ATPase-like fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 3

Expression of Recombinant ATPase-like Protein in COS Cells

To express the ATPase-like gene in COS cells, the pcDNA/Amp vector by Invitrogen Corporation (San Diego, Calif.) is used. This vector contains an SV40 origin of replication, an ampicillin resistance gene, an E. coli replication origin, a CMV promoter followed by a polylinker region, and an SV40 intron and polyadenylation site. A DNA fragment encoding the entire ATPase-like protein and an HA tag (Wilson et al. (1984) Cell 37:767) or a FLAG tag fused in-frame to its 3' end of the fragment is cloned into the polylinker region of the vector, thereby placing the expression of the recombinant protein under the control of the CMV promoter.

To construct the plasmid, the ATPase-like DNA sequence is amplified by PCR using two primers. The 5' primer contains the restriction site of interest followed by approximately twenty nucleotides of the ATPase-like coding sequence starting from the initiation codon; the 3' end sequence contains complementary sequences to the other restriction site of interest, a translation stop codon, the HA tag or FLAG tag and the last 20 nucleotides of the ATPase-like coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the ATPase-like gene is inserted in the correct orientation. The ligation mixture is transformed into E. coli cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the ATPase-like-pCDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual*. 2nd, ed., Cold Spring Harbor Laboratory, Cold Spring Harbor Laboratory Press, Cold Spring Harbor, N.Y., 1989. The expression of the ATPase-like polypeptide is detected by radiolabelling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, NY, 1988) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the ATPase-like coding sequence is cloned directly into the polylinker of the pCDNA/Amp vector using the appropriate restriction sites. The resulting plasmid is transfected into COS cells in the manner described above, and the expression of the ATPase-like polypeptide is detected by radiolabelling and immunoprecipitation using a ATPase-like specific monoclonal antibody.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated nucleic acid molecule selected from the group consisting of:
   a) a nucleic acid molecule comprising a fragment of at least 400 nucleotides of the nucleotide sequence of SEQ ID NO:1 or SEQ ID NO:3; and
   b) a nucleic acid molecule which encodes a fragment of a polypeptide comprising the amino acid sequence of SEQ ID NO:2, wherein the fragment comprises at least 100 contiguous amino acids of SEQ ID NO:2;
   wherein acid nucleic acid encodes a polypeptide having ATPase-like activity.

2. An isolated nucleic acid molecule selected from the group consisting of:
   a) a nucleic acid comprising the nucleotide sequence of SEQ ID NO:1, SEQ ID NO:3;
   b) a nucleic acid molecule which encodes a polypeptide comprising the amino acid sequence of SEQ ID NO:2; and
   c) a nucleic acid molecule comprising the complement of a) or b).

3. The nucleic acid molecule of claim 2 further comprising vector nucleic acid sequences.

4. The nucleic acid molecule of claim 2 further comprising nucleic acid sequences encoding a heterologous polypeptide.

5. A host cell which contains the nucleic acid molecule of claim 2.

6. The host cell of claim 5 which is a mammalian host cell.

7. A method for producing a polypeptide selected from the group consisting of:
   a) a polypeptide comprising the amino acid sequence of SEQ ID NO:2;
   b) a polypeptide comprising a fragment of the amino acid sequence of SEQ ID NO:2, wherein the fragment comprises at least 100 contiguous amino acids of SEQ ID NO:2; and,
   c) a biologically active polypeptide having at least 60% sequence identity to the polypeptide sequence of SEQ ID NO:2;
   comprising culturing a host cell containing a nucleic acid molecule that encodes said polypeptide under conditions in which the nucleic acid molecule is expressed, wherein acid polypeptide has ATPase-like activity.

8. The method of claim 7, wherein the polypeptide comprises the amino acid sequence of SEQ ID NO:2.

9. A method for detecting the presence of a nucleic acid molecule of claim 2 in a sample, comprising the steps of:
   a) contacting the sample with a nucleic acid probe or primer which selectively hybridizes to the nucleic acid molecule; and
   b) determining whether the nucleic acid probe or primer binds to a nucleic acid molecule in the sample.

10. The method of claim 9, wherein the sample comprises mRNA molecules and is contacted with a nucleic acid probe.

11. A kit comprising a compound which selectively hybridizes to a nucleic acid molecule of claim 2 and instructions for use.

12. An isolated nucleic acid molecule comprising a nucleotide sequence which is at least 60% identical to the nucleotide sequence of SEQ ID NO:1 or SEQ ID NO:3, wherein said sequence encodes a polypeptide having ATPase-like activity, or a complement thereof.

13. The nucleic acid molecule of claim 12, wherein the nucleotide sequence is at least 75% identical to the nucleotide sequence of SEQ ID NO:1 or SEQ ID NO:3, or a complement thereof.

14. The nucleic acid molecule of claim 12, wherein the nucleotide sequence is at least 85% identical to the nucleotide sequence of SEQ ID NO:1 or SEQ ID NO:3, or a complement thereof.

15. The nucleic acid molecule of claim 12, wherein the nucleotide sequence is at least 95% identical to the nucleotide sequence of SEQ ID NO:1 or SEQ ID NO:3, or a complement thereof.

16. The nucleic acid molecule of claim 12, wherein the nucleotide sequence is at least 98% identical to the nucleotide sequence of SEQ ID NO:1, or a complement thereof.

* * * * *

SEQUENCE LISTING

```
<160> NUMBER OF SEQ ID NOS: 4

<210> SEQ ID NO 1
<211> LENGTH: 1748
<212> TYPE: DNA
<213> ORGANISM: Homo sapiens
<220> FEATURE:
<221> NAME/KEY: CDS
<222> LOCATION: (79)...(1164)

<400> SEQUENCE: 1
ctatagggag tcgccccgcg tccgggccgg ctgagggcac ttgctcttgc tgtttctgcc        60
cctgggttaa cattcaag atg gta cat gct gaa gcc ttt tct cgt cct ttg       111
                    Met Val His Ala Glu Ala Phe Ser Arg Pro Leu
                     1               5                  10 agt cgg aat gaa gtt gtt ggt tta att ttc cgt ttg aca ata ttt ggt       159
Ser Arg Asn Glu Val Val Gly Leu Ile Phe Arg Leu Thr Ile Phe Gly
             15                  20                  25 gca gtg aca tac ttt act atc aaa tgg atg gta gat gca att gat cca       207
Ala Val Thr Tyr Phe Thr Ile Lys Trp Met Val Asp Ala Ile Asp Pro
         30                  35                  40
```

```
                                                          -continued acc aga aag caa aaa gta gaa gct cag aaa cag gca gaa aaa cta atg        255
Thr Arg Lys Gln Lys Val Glu Ala Gln Lys Gln Ala Glu Lys Leu Met
 45                  50                  55 aag caa att gga gtg aaa aat gtg aag ctc tca gaa tat gaa atg agt        303
Lys Gln Ile Gly Val Lys Asn Val Lys Leu Ser Glu Tyr Glu Met Ser
 60                  65                  70                  75 att gct gct cat ctt gta gac cct ctt aat atg cat gtt act tgg agt        351
Ile Ala Ala His Leu Val Asp Pro Leu Asn Met His Val Thr Trp Ser
                 80                  85                  90 gat ata gca ggt tta gat gat gtc att acg gat ctg aaa gac aca gtc        399
Asp Ile Ala Gly Leu Asp Asp Val Ile Thr Asp Leu Lys Asp Thr Val
                 95                 100                 105 atc tta cct atc aaa aag aaa cat ttg ttt gag aat tcc agg ctt ctg        447
Ile Leu Pro Ile Lys Lys Lys His Leu Phe Glu Asn Ser Arg Leu Leu
            110                 115                 120 cag cct cca aaa ggt gtt ctt ctc tat ggg cct cca ggc tgt ggt aaa        495
Gln Pro Pro Lys Gly Val Leu Leu Tyr Gly Pro Pro Gly Cys Gly Lys
            125                 130                 135 acg ttg att gcc aag gcc aca gcc aaa gaa gca ggc tgt cga ttt att        543
Thr Leu Ile Ala Lys Ala Thr Ala Lys Glu Ala Gly Cys Arg Phe Ile
140                 145                 150                 155 aac ctt cag cct tcg aca ctg acc gat aag tgg tat gga gaa tct cag        591
Asn Leu Gln Pro Ser Thr Leu Thr Asp Lys Trp Tyr Gly Glu Ser Gln
                160                 165                 170 aaa ttg gct gct gct gtc ttc tcc ctt gcc ata aag cta caa cca tcc        639
Lys Leu Ala Ala Ala Val Phe Ser Leu Ala Ile Lys Leu Gln Pro Ser
                175                 180                 185 atc atc ttt ata gat gaa ata gac tcc ttt cta cga aac cgt tca agt        687
Ile Ile Phe Ile Asp Glu Ile Asp Ser Phe Leu Arg Asn Arg Ser Ser
                190                 195                 200 tct gac cat gaa gct aca gcc atg atg aaa gct cag ttt atg agt ctc        735
Ser Asp His Glu Ala Thr Ala Met Met Lys Ala Gln Phe Met Ser Leu
205                 210                 215 tgg gat gga ttg gat act gat cac agc tgc cag gtc ata gta atg gga        783
Trp Asp Gly Leu Asp Thr Asp His Ser Cys Gln Val Ile Val Met Gly
220                 225                 230                 235 gct acc aat cgt cct cag gac ctt gac tcg gct ata atg aga aga atg        831
Ala Thr Asn Arg Pro Gln Asp Leu Asp Ser Ala Ile Met Arg Arg Met
                240                 245                 250 cct aca aga ttt cat atc aac cag cct gct tta aaa cag aga gaa gca        879
Pro Thr Arg Phe His Ile Asn Gln Pro Ala Leu Lys Gln Arg Glu Ala
                255                 260                 265 atc ctg aaa ctc atc ttg aaa aat gaa aat gtg gat agg cat gta gac        927
Ile Leu Lys Leu Ile Leu Lys Asn Glu Asn Val Asp Arg His Val Asp
                270                 275                 280 ctg cta gaa gtt gcc cag gaa act gat ggg ttt tca gga agt gac cta        975
Leu Leu Glu Val Ala Gln Glu Thr Asp Gly Phe Ser Gly Ser Asp Leu
285                 290                 295 aaa gag atg tgt cga gat gct gcc ctc ctc tgt gtt aga gaa tat gtt       1023
Lys Glu Met Cys Arg Asp Ala Ala Leu Leu Cys Val Arg Glu Tyr Val
300                 305                 310                 315 aat tct aca tca gaa gaa agc cat gac gaa gat gaa att cgg cct gtt       1071
Asn Ser Thr Ser Glu Glu Ser His Asp Glu Asp Glu Ile Arg Pro Val
                320                 325                 330 caa cag cag gac ctg cat cgg gca att gaa aag atg aag aaa tca aag       1119
Gln Gln Gln Asp Leu His Arg Ala Ile Glu Lys Met Lys Lys Ser Lys
                335                 340                 345 gat gca gca ttt cag aat gtt tta aca cat gtt tgt tta gat taa           1164
Asp Ala Ala Phe Gln Asn Val Leu Thr His Val Cys Leu Asp  *
                350                 355                 360
```

```
gagtaaagat catttgtaca gttcagtgat ctagtttggt gtgtcctctt atcagttagt    1224
ggaaatagaa cggaaagagt gctctttaaa caatgaggga gctcagtgtt tatggtttta    1284
tactctgaat tctaagttat tgagatatag ttgttacata ggtggtatta ctgttggtca    1344
aaaatcatga ggaggaacag ttgaatccag cctgaacgtg ggtgcttgtg tttgaccttt    1404
tcagccatat attgtacagc cttatagaat ctaagctggt cttaaagtca taaatgattc    1464
attgggtcat tagtgagaaa cggggatgtg gttaggtgct ggttcctaga catgtgagta    1524
tgcgtttgtg tgtgtgcgtg tatgtatgtg tatattaaat gtatatatcc acacatttta    1584
tattgacatt ctgtagatat gtttgaatat agaaactttt tttaccccaa ctactgaatc    1644
caggagtacc aaataatata tagtaaaact aagatttaag gttgtgtcaa aaaggtacag    1704
tggattcagc catttccatt tgtcatttgt ttcaaccttt ttta                     1748
```

<210> SEQ ID NO 2
<211> LENGTH: 361
<212> TYPE: PRT
<213> ORGANISM: Homo sapiens

<400> SEQUENCE: 2

```
Met Val His Ala Glu Ala Phe Ser Arg Pro Leu Ser Arg Asn Glu Val
 1               5                  10                  15

Val Gly Leu Ile Phe Arg Leu Thr Ile Phe Gly Ala Val Thr Tyr Phe
            20                  25                  30

Thr Ile Lys Trp Met Val Asp Ala Ile Asp Pro Thr Arg Lys Gln Lys
        35                  40                  45

Val Glu Ala Gln Lys Gln Ala Glu Lys Leu Met Lys Gln Ile Gly Val
    50                  55                  60

Lys Asn Val Lys Leu Ser Glu Tyr Glu Met Ser Ile Ala Ala His Leu
65                  70                  75                  80

Val Asp Pro Leu Asn Met His Val Thr Trp Ser Asp Ile Ala Gly Leu
                85                  90                  95

Asp Asp Val Ile Thr Asp Leu Lys Asp Thr Val Ile Leu Pro Ile Lys
            100                 105                 110

Lys Lys His Leu Phe Glu Asn Ser Arg Leu Leu Gln Pro Pro Lys Gly
        115                 120                 125

Val Leu Leu Tyr Gly Pro Pro Gly Cys Gly Lys Thr Leu Ile Ala Lys
    130                 135                 140

Ala Thr Ala Lys Glu Ala Gly Cys Arg Phe Ile Asn Leu Gln Pro Ser
145                 150                 155                 160

Thr Leu Thr Asp Lys Trp Tyr Gly Glu Ser Gln Lys Leu Ala Ala Ala
                165                 170                 175

Val Phe Ser Leu Ala Ile Lys Leu Gln Pro Ser Ile Ile Phe Ile Asp
            180                 185                 190

Glu Ile Asp Ser Phe Leu Arg Asn Arg Ser Ser Ser Asp His Glu Ala
        195                 200                 205

Thr Ala Met Met Lys Ala Gln Phe Met Ser Leu Trp Asp Gly Leu Asp
    210                 215                 220

Thr Asp His Ser Cys Gln Val Ile Val Met Gly Ala Thr Asn Arg Pro
225                 230                 235                 240

Gln Asp Leu Asp Ser Ala Ile Met Arg Arg Met Pro Thr Arg Phe His
                245                 250                 255

Ile Asn Gln Pro Ala Leu Lys Gln Arg Glu Ala Ile Leu Lys Leu Ile
            260                 265                 270
```

Leu Lys Asn Glu Asn Val Asp Arg His Val Asp Leu Leu Glu Val Ala
            275                 280                 285

Gln Glu Thr Asp Gly Phe Ser Gly Ser Asp Leu Lys Glu Met Cys Arg
        290                 295                 300

Asp Ala Ala Leu Leu Cys Val Arg Glu Tyr Val Asn Ser Thr Ser Glu
305                 310                 315                 320

Glu Ser His Asp Glu Asp Glu Ile Arg Pro Val Gln Gln Gln Asp Leu
                325                 330                 335

His Arg Ala Ile Glu Lys Met Lys Lys Ser Lys Asp Ala Ala Phe Gln
            340                 345                 350

Asn Val Leu Thr His Val Cys Leu Asp
            355                 360

<210> SEQ ID NO 3
<211> LENGTH: 1086
<212> TYPE: DNA
<213> ORGANISM: Homo sapiens

<400> SEQUENCE: 3
atggtacatg ctgaagcctt ttctcgtcct ttgagtcgga atgaagttgt tggtttaatt      60
ttccgtttga caatatttgg tgcagtgaca tactttacta tcaaatggat ggtagatgca     120
attgatccaa ccagaaagca aaagtagaa gctcagaaac aggcagaaaa actaatgaag      180
caaattggag tgaaaaatgt gaagctctca gaatatgaaa tgagtattgc tgctcatctt     240
gtagaccctc ttaatatgca tgttacttgg agtgatatag caggtttaga tgatgtcatt     300
acggatctga agacacagt catcttacct atcaaaaaga acatttgtt tgagaattcc      360 aggcttctgc agcctccaaa aggtgttctt ctctatgggc ctccaggctg tggtaaaacg     420
ttgattgcca aggccacagc caagaagca ggctgtcgat ttattaacct tcagccttcg      480
acactgaccg ataagtggta tggagaatct cagaaattgg ctgctgctgt cttctccctt     540
gccataaagc tacaaccatc catcatcttt atagatgaaa tagactcctt tctacgaaac     600
cgttcaagtt ctgaccatga agctacagcc atgatgaaag ctcagtttat gagtctctgg     660
gatggattgg atactgatca cagctgccag gtcatagtaa tgggagctac caatcgtcct     720
caggaccttg actcggctat aatgagaaga atgcctacaa gatttcatat caaccagcct     780
gctttaaaac agagagaagc aatcctgaaa ctcatcttga aaaatgaaaa tgtggatagg     840
catgtagacc tgctagaagt tgcccaggaa actgatgggt tttcaggaag tgacctaaaa     900
gagatgtgtc gagatgctgc cctcctctgt gttagagaat atgttaattc tacatcagaa     960
gaaagccatg acgaagatga aattcggcct gttcaacagc aggacctgca tcgggcaatt    1020
gaaaagatga agaaatcaaa ggatgcagca tttcagaatg tttttaacaca tgtttgttta    1080 gattaa                                                                1086

<210> SEQ ID NO 4
<211> LENGTH: 220
<212> TYPE: PRT
<213> ORGANISM: Artificial Sequence
<220> FEATURE:
<223> OTHER INFORMATION: consensus sequence for the AAA domain

<400> SEQUENCE: 4

Gly Val Leu Leu Tyr Gly Pro Pro Gly Thr Gly Lys Thr Leu Leu Ala
  1               5                  10                  15

Lys Ala Val Ala Asn Glu Leu Gly Ser Leu Arg Lys Ala Pro Phe Ile

```
                    20                  25                  30
Ser Ile Ser Gly Tyr Ser Glu Leu Val Ser Lys Tyr Val Gly Glu Ser
            35                  40                  45

Glu Lys Arg Val Arg Ala Leu Phe Glu Leu Ala Arg Glu Leu Arg Lys
    50                  55                  60

Arg Ala Ala Pro Cys Pro Ile Ile Phe Ile Asp Glu Ile Asp Ala Ile
65                  70                  75                  80

Ala Pro Lys Arg Gly Gly Glu Val Ser Arg Arg Val Val Asn Gln Leu
                85                  90                  95

Leu Thr Glu Met Asp Leu Glu Arg Ala Gly Phe Ser Lys Asn Ser Ser
                100                 105                 110

Arg Gly Glu Asp Thr Ile Asp Leu Ser Asn Val Leu Val Ile Ala Ala
            115                 120                 125

Thr Asn Arg Pro Asp Thr Leu Asp Pro Ala Leu Leu Arg Pro Gly Arg
    130                 135                 140

Phe Asp Arg Glu Ile Glu Ile Pro Leu Pro Pro Asp Glu Glu Gly Arg
145                 150                 155                 160

Leu Asp Ile Leu Lys Ile His Leu Lys Lys Met Pro Leu Ser Ser Ser
                165                 170                 175

Leu Lys Gln Ser Glu Leu Ala Glu Asp Val Asp Leu Asp Glu Leu Ala
                180                 185                 190

Glu Glu Ile Ala Thr Arg Thr Glu Gly Phe Ser Gly Ala Asp Leu Lys
            195                 200                 205

Ala Leu Cys Arg Glu Ala Ala Leu Arg Ala Ile Arg
        210                 215                 220
```